(12) United States Patent
Ikeuchi

(10) Patent No.: US 10,273,289 B2
(45) Date of Patent: *Apr. 30, 2019

(54) COMPOSITE COMPRISING ANTIBODY CAPABLE OF BINDING TO INTRANUCLEAR PROTEIN OF INFLUENZA VIRUS

(71) Applicant: PANASONIC INTELLECTUAL PROPERTY MANAGEMENT CO., LTD., Osaka (JP)

(72) Inventor: Emina Ikeuchi, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,563

(22) Filed: May 3, 2018

(65) Prior Publication Data

US 2018/0251528 A1 Sep. 6, 2018

Related U.S. Application Data

(63) Continuation of application No. 15/649,279, filed on Jul. 13, 2017, now Pat. No. 9,988,436, which is a continuation-in-part of application No. 15/296,194, filed on Oct. 18, 2016, now abandoned.

(60) Provisional application No. 62/344,161, filed on Jun. 1, 2016.

(51) Int. Cl.
| | |
|---|---|
| *C12N 5/00* | (2006.01) |
| *C12Q 1/70* | (2006.01) |
| *C07K 16/10* | (2006.01) |
| *C12N 5/07* | (2010.01) |
| *A61K 39/00* | (2006.01) |
| *C07K 16/00* | (2006.01) |

(52) U.S. Cl.
CPC ............ *C07K 16/1018* (2013.01); *C12N 5/06* (2013.01); *C12Q 1/70* (2013.01); *A01K 2217/075* (2013.01); *A61K 2039/505* (2013.01); *C07K 16/00* (2013.01); *C07K 2317/21* (2013.01); *C07K 2317/22* (2013.01); *C07K 2317/569* (2013.01); *C12N 5/00* (2013.01)

(58) Field of Classification Search
None
See application file for complete search history.

(56) References Cited

U.S. PATENT DOCUMENTS

2014/0302063 A1 10/2014 Hufton

FOREIGN PATENT DOCUMENTS

| CN | 103804493 A | 5/2014 |
|---|---|---|
| WO | 94/09136 A1 | 4/1994 |

OTHER PUBLICATIONS

Wei et al., Potent Neutralization of Influenza A Virus by a Single-Domain Antibody Blocking M2 Ion Channel Protein, 2011, PLoS ONE, vol. 6, Issue 12, pp. 1-11.*
Non-Final Office Action issued in U.S. Appl. No. 15/649,279 dated Dec. 14, 2017.
Notice of Allowance issued in U.S. Appl. No. 15/649,279, dated Feb. 12, 2018.
Non-Final Office Action issued in U.S. Appl. No. 15/296,194 dated Dec. 7, 2016.
Non-Final Office Action issued in U.S. Appl. No. 15/296,194 dated Mar. 28, 2017.
Simon E. Hufton et. al., "The Breadth of Cross Sub-Type Neutralisation Activity of a Single Domain Antibody to Influenza Hemagglutinin Can Be Increased by Antibody Valency", PLOS ONE [www.plosone.org], Aug. 2014, vol. 9, Issue 8, e103294, pp. 1-19.
Rivera et al., Serologic survey of viral antibodies in the Peruvian alpaca (*Lama pacos*), 1987, American Journal of Veterinary Research, vol. 48, No. 2, pp. 189-191 (abstract provided).
Vajdos et al. Comprehensive Functional Maps of the Antigenbinding Site of an Anti-ErbB2 Antibody Obtained with Shotgun Scanning Mutagenesis, 2002, Journal of Molecular Biology, vol. 320, pp. 415-428.
Hanke, L. et al. "The Antiviral Mechanism of an Influenza a Virus Nucleoprotein-Specific Single-Domain Antibody Fragment," American Society for Microbiology, vol. 7, Issue 6, Nov./Dec. 2016; pp. 1-11; downloaded from mbio.asm.org on Dec. 11, 2017—Published by mbio.asm.org.
Final Office Action issued in U.S. Appl. No. 15/296,194, dated Mar. 28, 2017.

* cited by examiner

*Primary Examiner* — Benjamin P Blumel
(74) *Attorney, Agent, or Firm* — McDermott Will & Emery LLP

(57) ABSTRACT

The present invention provides a composite comprising a novel antibody and at least one selected from the group consisting of a solid phase support and a labeled substance. The antibody consists of the amino acid sequence represented by SEQ ID NO: 08, and is capable of binding to an intranuclear protein of an influenza virus type A. The influenza virus type A is at least one selected from the group consisting of H1N1, H2N2, H3N2, and H7N9. The antibody is bound to the at least one selected from the group consisting of the solid phase support and the labeled substance. The present invention also provides a detection device and a detection method using the composite.

4 Claims, 16 Drawing Sheets

Specification includes a Sequence Listing.

SEQUENCE LISTING

```
<160> NUMBER OF SEQ ID NOS: 25

<210> SEQ ID NO 1
<211> LENGTH: 10
<212> TYPE: PRT
<213> ORGANISM: Lama pacos

<400> SEQUENCE: 1

Arg Thr Ile Phe Asn Pro Asn Val Met Gly
1               5                   10

<210> SEQ ID NO 2
<211> LENGTH: 16
<212> TYPE: PRT
<213> ORGANISM: Lama pacos

<400> SEQUENCE: 2

Asp Ile Ser Leu Ser Gly Ser Thr Asn Tyr Ala Asp Ser Val Lys Gly
1               5                   10                  15

<210> SEQ ID NO 3
<211> LENGTH: 10
<212> TYPE: PRT
<213> ORGANISM: Lama pacos

<400> SEQUENCE: 3

Asn Ala Ile Ser Gly Ala Pro Gly Arg Tyr
1               5                   10

<210> SEQ ID NO 4
<211> LENGTH: 25
<212> TYPE: PRT
<213> ORGANISM: Lama pacos

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 5
<211> LENGTH: 14
<212> TYPE: PRT
<213> ORGANISM: Lama pacos

<400> SEQUENCE: 5

Trp Tyr Arg Gln Ala Pro Gly Lys Gln Arg Glu Leu Val Ala
1               5                   10

<210> SEQ ID NO 6
```

```
<211> LENGTH: 32
<212> TYPE: PRT
<213> ORGANISM: Lama pacos

<400> SEQUENCE: 6

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Asn Thr
            20                  25                  30

<210> SEQ ID NO 7
<211> LENGTH: 11
<212> TYPE: PRT
<213> ORGANISM: Lama pacos

<400> SEQUENCE: 7

Trp Gly Gln Gly Ala Gln Val Thr Val Ser Ser
1               5                   10

<210> SEQ ID NO 8
<211> LENGTH: 118
<212> TYPE: PRT
<213> ORGANISM: Lama pacos

<400> SEQUENCE: 8

Gln Val Gln Leu Val Glu Ser Gly Gly Leu Val Gln Ala Gly Gly
1               5                   10                  15

Ser Leu Arg Leu Ser Cys Ala Ala Ser Arg Thr Ile Phe Asn Pro Asn
            20                  25                  30

Val Met Gly Trp Tyr Arg Gln Ala Pro Gly Lys Gln Arg Glu Leu Val
        35                  40                  45

Ala Asp Ile Ser Leu Ser Gly Ser Thr Asn Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Thr Asn Ala Ile Ser Gly Ala Pro Gly Arg Tyr Trp Gly Gln Gly Thr
            100                 105                 110

Gln Val Thr Val Ser Ser
        115

<210> SEQ ID NO 9
<211> LENGTH: 15
<212> TYPE: DNA
<213> ORGANISM: Artificial Sequence
<220> FEATURE:
<223> OTHER INFORMATION: Synthesized Primer

<400> SEQUENCE: 9
ggtggtcctg gctgc                                                    15

<210> SEQ ID NO 10
<211> LENGTH: 50
<212> TYPE: DNA
<213> ORGANISM: Artificial Sequence
<220> FEATURE:
<223> OTHER INFORMATION: Synthesized Primer

<400> SEQUENCE: 10
ctgctcctcg cggcccagcc ggccatggct sagktgcagc tcgtggagtc              50
```

<210> SEQ ID NO 11
<211> LENGTH: 21
<212> TYPE: DNA
<213> ORGANISM: Artificial Sequence
<220> FEATURE:
<223> OTHER INFORMATION: Synthesized Primer

<400> SEQUENCE: 11
tggggtcttc gctgtggtgc g                                     21

<210> SEQ ID NO 12
<211> LENGTH: 21
<212> TYPE: DNA
<213> ORGANISM: Artificial Sequence
<220> FEATURE:
<223> OTHER INFORMATION: Synthesized Primer

<400> SEQUENCE: 12
ttgtggtttt ggtgtcttgg g                                     21

<210> SEQ ID NO 13
<211> LENGTH: 45
<212> TYPE: DNA
<213> ORGANISM: Artificial Sequence
<220> FEATURE:
<223> OTHER INFORMATION: Synthesized Primer

<400> SEQUENCE: 13
tttgctctgc ggccgcagag gccgtggggt cttcgctgtg gtgcg           45

<210> SEQ ID NO 14
<211> LENGTH: 46
<212> TYPE: DNA
<213> ORGANISM: Artificial Sequence
<220> FEATURE:
<223> OTHER INFORMATION: Synthesized Primer

<400> SEQUENCE: 14
tttgctctgc ggccgcagag gccgattgtg gttttggtgt cttggg          46

<210> SEQ ID NO 15
<211> LENGTH: 13
<212> TYPE: DNA
<213> ORGANISM: Artificial Sequence
<220> FEATURE:
<223> OTHER INFORMATION: Synthesized DNA which represents SfiI(a) site

<400> SEQUENCE: 15
ggcccagccg gcc                                              13

<210> SEQ ID NO 16
<211> LENGTH: 13
<212> TYPE: DNA
<213> ORGANISM: Artificial Sequence
<220> FEATURE:
<223> OTHER INFORMATION: Synthesized DNA which represents SfiI(b) site

<400> SEQUENCE: 16
ggcctctgcg gcc                                              13

<210> SEQ ID NO 17
<211> LENGTH: 4057
<212> TYPE: DNA
<213> ORGANISM: Artificial Sequence
<220> FEATURE:
<223> OTHER INFORMATION: Synthesized plamid Vector 1

<400> SEQUENCE: 17

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attcccttt     240
ttgcggcatt ttgccttcct gttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttttaatt taaaaggatc taggtgaaga    1140
tcctttttga taatctcatg accaaaatcc cttaacgtga gttttcgttc cactgagcgt    1200
cagaccccgt agaaaagatc aaaggatctt cttgagatcc ttttttttctg cgcgtaatct    1260
gctgcttgca acaaaaaaa ccaccgctac cagcggtggt ttgtttgccg gatcaagagc    1320
taccaactct ttttccgaag gtaactggct tcagcagagc gcagatacca atactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg tcgggctga acgggggtt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag    1800
gggggcggag cctatggaaa aacgccagca acgcggcctt tttacggttc ctggccttt    1860
gctggccttt tgctcacatg ttctttcctg cgttatcccc tgattctgtg ataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt cgaaggagac agtcataatg aaatacctgc tgccgaccgc    2280
```

```
tgctgctggt ctgctgctcc tcgcggccca gccggccatg gagctcaaga tgacacagac    2340
tacatcctcc ctgtcagcct ctctgggaga cagagtcacc atcagttgca gggcaagtca    2400
ggacattagc gattatttaa actggtatca gcagaaacca gatggaactg ttaaactcct    2460
gatctattac acatcaagtt tacactcagg agtcccatca aggttcagtg gcggtgggtc    2520
tggaacagat tattctctca ccattagcaa cctggagcaa gaagatattg ccacttactt    2580
ttgccaacag ggtaatacgc ttccgtggac gtttggtgga ggcaccaagc tggaaatcaa    2640
acgggctgat gctgcaccaa ctgtaggcct ctgcggccgc agagcaaaaa ctcatctcag    2700
aagaggatct gaatgggccg cataggggtt ccggtgattt tgattatgaa agatggcaa     2760 acgctaataa gggggctatg accgaaaatg ccgatgaaaa cgcgctacag tctgacgcta    2820
aaggcaaact tgattctgtc gctactgatt acggtgctgc tatcgatggt ttcattggtg    2880
acgtttccgg ccttgctaat ggtaatggtg ctactggtga ttttgctggc tctaattccc    2940
aaatggctca gtcggtgac  ggtgataatt caccttaat  gaataatttc cgtcaatatt    3000
taccttccct ccctcaatcg gttgaatgtc gcccttttgt ctttagcgct ggtaaaccat    3060
atgaattttc tattgattgt gacaaaataa acttattccg tggtgtcttt gcgtttcttt    3120
tatatgttgc caccttatg  tatgtatttt ctacgtttgc taacatactg cgtaataagg    3180
agtcttaata agaattcact ggccgtcgtt ttacaacgtc gtgactggga aaaccctggc    3240
gttacccaac ttaatcgcct tgcagcacat cccccttcg  ccagctggcg taatagcgaa    3300
gaggcccgca ccgatcgccc ttcccaacag ttgcgcagcc tgaatggcga atggcgcctg    3360
atgcggtatt ttctccttac gcatctgtgc ggtatttcac accgcatatg aaaattgtaa    3420
gcgttaatat tttgttaaaa ttcgcgttaa attttgtta  aatcagctca ttttttaacc    3480
aataggccga aatcggcaaa atcccttata aatcaaaaga atagaccgag atagggttga    3540
gtgttgttcc agtttggaac aagagtccac tattaaagaa cgtggactcc aacgtcaaag    3600
ggcgaaaaac cgtctatcag gcgatggcc  cactacgtga accatcaccc taatcaagtt    3660
ttttggggtc gaggtgccgt aaagcactaa atcggaaccc taaagggagc cccgatttta   3720
gagcttgacg gggaaagccg gcgaacgtgg cgagaaagga agggaagaaa gcgaaaggag    3780
cgggcgctag ggcgctggca agtgtagcgg tcacgctgcg cgtaaccacc acacccgccg    3840
cgcttaatgc gccgctacag ggcgcgtccc atatggtgca ctctcagtac aatctgctct    3900
gatgccgcat agttaagcca gccccgacac ccgccaacac ccgctgacgc gccctgacgg    3960
gcttgtctgc tcccggcatc cgcttacaga caagctgtga ccgtctccgg gagctgcatg    4020
tgtcagaggt tttcaccgtc atcaccgaaa cgcgcga                            4057
```

<210> SEQ ID NO 18
<211> LENGTH: 357
<212> TYPE: DNA
<213> ORGANISM: Artificial Sequence
<220> FEATURE:
<223> OTHER INFORMATION: Synthesized DNA coding for VHH antibody

<400> SEQUENCE: 18

```
gctcaggtgc agctcgtgga gtctggggga ggcttggtgc aggctggggg gtctctgaga     60
ctctcctgtg cagcctctcg aaccatcttc aatccgaatg tcatgggctg gtaccgccag    120
gctccaggga agcagcgcga gttggtcgca gatattagtt taagtggcag cacaaactat    180
gcagactccg tgaagggccg attcacgatc tccagagaca cgccaagaa  cacgatgtat    240 ctgcaaatga acagcctgaa gcctgaggat acagccgtct attattgtaa tactaatgcg    300
```

```
atcagcggtg cgcccggaag gtactggggc cagggggaccc aggtcaccgt ctcctca        357
```

<210> SEQ ID NO 19
<211> LENGTH: 38
<212> TYPE: DNA
<213> ORGANISM: Artificial Sequence
<220> FEATURE:
<223> OTHER INFORMATION: Synthesized Primer

<400> SEQUENCE: 19

```
cagccggcca tggctgctca ggtgcagctc gtggagtc                              38
```

<210> SEQ ID NO 20
<211> LENGTH: 38
<212> TYPE: DNA
<213> ORGANISM: Artificial Sequence
<220> FEATURE:
<223> OTHER INFORMATION: Synthesized Primer

<400> SEQUENCE: 20

```
atggtggcgg ccgcgtgagg agacggtgac ctgggtcc                              38
```

<210> SEQ ID NO 21
<211> LENGTH: 387
<212> TYPE: DNA
<213> ORGANISM: Artificial Sequence
<220> FEATURE:
<223> OTHER INFORMATION: a DNA containing a gene sequence coding for the
      amino acid sequence represented by SEQ ID NO: 08

<400> SEQUENCE: 21

```
cagccggcca tggctgctca ggtgcagctc gtggagtctg ggggaggctt ggtgcaggct      60 gggggggtctc tgagactctc ctgtgcagcc tctcgaacca tcttcaatcc gaatgtcatg    120
ggctggtacc gccaggctcc agggaagcag cgcgagttgg tcgcagatat tagtttaagt    180
ggcagcacaa actatgcaga ctccgtgaag ggccgattca cgatctccag agacaacgcc    240
aagaacacga tgtatctgca aatgaacagc ctgaagcctg aggatacagc cgtctattat    300
tgtaatacta atgcgatcag cggtgcgccc ggaaggtact ggggccaggg gacccaggtc    360
accgtctcct cacgcggccg ccaccat                                         387
```

<210> SEQ ID NO 22
<211> LENGTH: 33
<212> TYPE: DNA
<213> ORGANISM: Artificial Sequence
<220> FEATURE:
<223> OTHER INFORMATION: Synthesized Primer

<400> SEQUENCE: 22

```
cgcggccgcc accatcatca ccaccattaa tag                                  33
```

<210> SEQ ID NO 23
<211> LENGTH: 31
<212> TYPE: DNA
<213> ORGANISM: Artificial Sequence
<220> FEATURE:
<223> OTHER INFORMATION: Synthesized Primer

<400> SEQUENCE: 23

```
agccatggcc ggctgggccg cgagtaataa c                                    31
```

<210> SEQ ID NO 24
<211> LENGTH: 498

<212> TYPE: PRT
<213> ORGANISM: Influenza A virus

<400> SEQUENCE: 24

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400
```

```
Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

<210> SEQ ID NO 25
<211> LENGTH: 3096
<212> TYPE: DNA
<213> ORGANISM: Artificial Sequence
<220> FEATURE:
<223> OTHER INFORMATION: a DNA obtained by amplifying a part of Vector pRA2

<400> SEQUENCE: 25

```
cgcggccgcc accatcatca ccaccattaa tagcactagt caagaggatc cggctgctaa      60
caaagcccga aaggaagctg agttggctgc tgccaccgct gagcaataac tagcataacc    120
ccttggggcc tctaaacggg tcttgagggg ttttttgctg aaaggaggaa ctatatccgg    180
atgaattccg tgtattctat agtgtcacct aaatcgtatg tgtatgatac ataaggttat    240
gtattaattg tagccgcgtt ctaacgacaa tatgtacaag cctaattgtg tagcatctgg    300
cttactgaag cagaccctat catctctctc gtaaactgcc gtcagagtcg gtttggttgg    360
acgaaccttc tgagtttctg gtaacgccgt cccgcacccg gaaatggtca gcgaaccaat    420
cagcagggtc atcgctagcc agatcctcta cgccggacgc atcgtggccg gcatcaccgg    480
cgccacaggt gcggttgctg gcgcctatat cgccgacatc accgatgggg aagatcgggc    540
tcgccacttc gggctcatga gcgcttgttt cggcgtgggt atggtggcag gccccgtggc    600
cggggggactg ttgggcgcca tctccttgca tgcaccattc cttgcggcgg cggtgctcaa    660
cggcctcaac ctactactgg gctgcttcct aatgcaggag tcgcataagg gagagcgtcg    720
aatggtgcac tctcagtaca atctgctctg atgccgcata gttaagccag ccccgacacc    780
cgccaacacc cgctgacgcg ccctgacggg cttgtctgct cccggcatcc gcttacagac    840
aagctgtgac cgtctccggg agctgcatgt gtcagaggtt ttccaccgtca tcaccgaaac    900
gcgcgagacg aaagggcctc gtgatacgcc tatttttata ggttaatgtc atgataataa    960
tggtttctta cacgtcaggt ggcacttttc ggggaaatgt gcgcggaacc cctatttgtt   1020
tattttctta aatacattca aatatgtatc cgctcatgag acaataaccc tgataaatgc   1080
ttcaataata ttgaaaaagg aagagtatga gtattcaaca tttccgtgtc gcccttattc   1140
ccttttttgc ggcattttgc cttcctgttt ttgctcaccc agaaacgctg gtgaaagtaa   1200
aagatgctga agatcagttg ggtgcacgag tgggttacat cgaactggat ctcaacagcg   1260
gtaagatcct tgagagtttt cgccccgaag aacgttttcc aatgatgagc acttttaaag   1320
ttctgctatg tggcgcggta ttatcccgta ttgacgccgg gcaagagcaa ctcggtcgcc   1380
gcatacacta ttctcagaat gacttggttg agtactcacc agtcacagaa aagcatctta   1440
```

-continued

```
cggatggcat gacagtaaga gaattatgca gtgctgccat aaccatgagt gataacactg    1500
cggccaactt acttctgaca acgatcggag gaccgaagga gctaaccgct tttttgcaca    1560
acatggggga tcatgtaact cgccttgatc gttgggaacc ggagctgaat gaagccatac    1620
caaacgacga gcgtgacacc acgatgcctg tagcaatggc aacaacgttg cgcaaactat    1680
taactggcga actacttact ctagcttccc ggcaacaatt aatagactgg atggaggcgg    1740
ataaagttgc aggaccactt ctgcgctcgg cccttccggc tggctggttt attgctgata    1800
aatctggagc cggtgagcgt gggtctcgcg gtatcattgc agcactgggg ccagatggta    1860
agccctcccg tatcgtagtt atctacacga cggggagtca ggcaactatg gatgaacgaa    1920
atagacagat cgctgagata ggtgcctcac tgattaagca ttggtaactg tcagaccaag    1980
tttactcata tactttag attgatttaa aacttcattt ttaatttaaa aggatctagg      2040
tgaagatcct ttttgataat ctcatgacca aaatcccta acgtgagttt tcgttccact      2100
gagcgtcaga ccccgtagaa aagatcaaag gatccttttg agatcctttt tttctgcgcg    2160
taatctgctg cttgcaaaca aaaaaaccac cgctaccagc ggtggtttgt ttgccggatc    2220
aagagctacc aactcttttt ccgaaggtaa ctggcttcag cagagcgcag ataccaaata    2280
ctgttcttct agtgtagccg tagttaggcc accacttcaa gaactctgta gcaccgccta    2340
catacctcgc tctgctaatc ctgttaccag tggctgctgc cagtgcgat aagtcgtgtc     2400 ttaccgggtt ggactcaaga cgatagttac cggataaggc gcagcggtcg ggctgaacgg    2460
ggggttcgtg cacacagccc agcttggagc gaacgaccta caccgaactg agatacctac    2520
agcgtgagct atgagaaagc gccacgcttc ccgaagggag aaaggcggac aggtatccgg    2580
taagcggcag ggtcggaaca ggagagcgca cgagggagct tccaggggga aacgcctggt    2640
atctttatag tcctgtcggg tttcgccacc tctgacttga gcgtcgattt ttgtgatgct    2700
cgtcaggggg gcggagccta tggaaaaacg ccagcaacgc ggcctttta cggttcctgg     2760 ccttttgctg gccttttgct cacatgttct ttcctgcgtt atccctgat tctgtggata     2820 accgtattac cgcctttgag tgagctgata ccgctcgccg cagccgaacg accgagcgca    2880
gcgagtcagt gagcgaggaa gcggaagagc gcccaatacg caaaccgcct ctccccgcgc    2940
gttggccgat tcattaatgc agctggctta tcgaaattaa tacgactcac tatagggaga    3000
cccaagcttt atttcaagga gacagtcata atgaaatacc tattgcctac ggcagccgct    3060
ggattgttat tactcgcggc ccagccggcc atggct                              3096
```

COMPOSITE COMPRISING ANTIBODY CAPABLE OF BINDING TO INTRANUCLEAR PROTEIN OF INFLUENZA VIRUS

CROSS-REFERENCE TO RELATED APPLICATIONS

This is a Continuation of U.S. patent application Ser. No. 15/649,279, filed on Jul. 13, 2017, which is a continuation-in-part of U.S. application Ser. No. 15/296,194, with a filing date of Oct. 18, 2016, which in turn claims priority of Provisional Patent Application Ser. No. 62/344,161, which was filed on Jun. 1, 2016, the contents of which Applications are hereby incorporated by reference.

INCORPORATION BY REFERENCE SEQUENCE LISTING

The material contained in the ASCII text file named "P0625743US03_ST25.txt" created on May 31, 2017, and having a file size of 20,747 bytes is incorporated by reference herein.

BACKGROUND

1. Technical Field

The present invention relates to a composite comprising an antibody capable of binding to an intranuclear protein of an influenza virus. The present invention also relates to a detection device and a detection method using the composite.

2. Description of the Related Art

Patent Literature 1 discloses antibodies each capable of binding to an influenza virus. At least a part of the antibodies disclosed in Patent Literature 1 are derived from an alpaca. Patent Literature 1 is incorporated herein by reference.

CITATION LIST

Patent Literature

United States Patent Application Publication No. 2014/0302063

SUMMARY

An object of the present invention is to provide a composite comprising a novel antibody capable of binding to an intranuclear protein of an influenza virus. Another object of the present invention is to provide a detection device and a detection method using the composite comprising the novel antibody.

The present invention is a composite, comprising:
an antibody; and
at least one selected from the group consisting of a sol id phase support and a labeled substance,
wherein
the antibody consists of the amino acid sequence represented by SEQ ID NO: 08, and is capable of binding to an intranuclear protein of an influenza virus type A;
the influenza virus type A is at least one selected from the group consisting of H1N1, H2N2, H3N2, and H7N9; and
the antibody is bound to the at least one selected from the group consisting of a solid phase support and the labeled substance.

The present invention provides a novel antibody capable of binding to an intranuclear protein of an influenza virus. The present invention also provides a detection device and a detection method using the composite comprising the novel antibody.

DETAILED DESCRIPTION OF THE EMBODIMENT

Figure 1A:
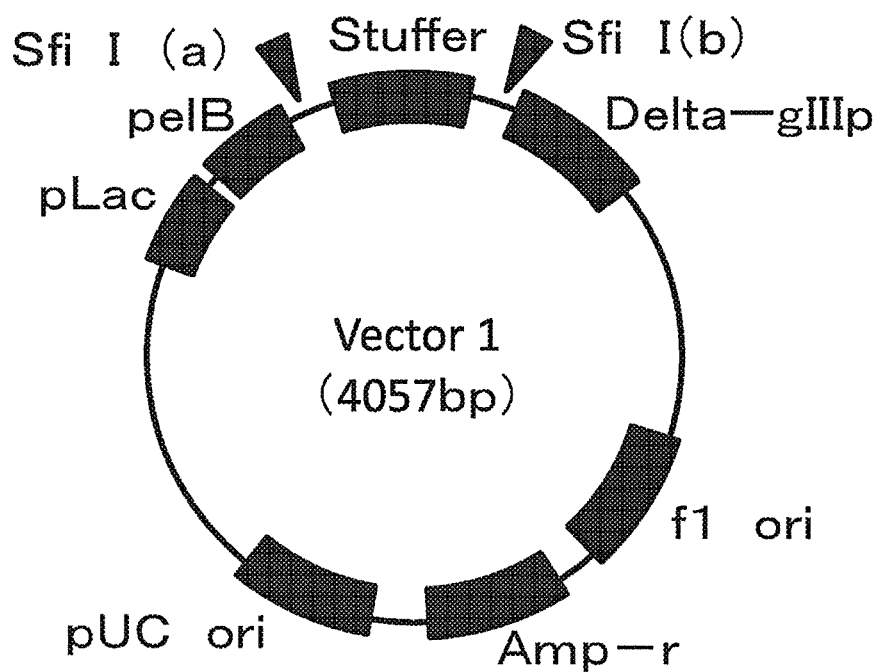
FIG. 1A is a map of a vector used to ligate various genes included in a gene library of a VHH antibody.

The antibody according to the present invention is capable of binding to an influenza virus type A. In particular, the antibody according to the present invention is capable of binding to an intranuclear protein of an influenza virus type A. As disclosed in Patent Literature 1, an antibody capable of binding to an influenza virus consists of, in an N- to C-direction, the following structural domains.

N-FR1-CDR1-FR2-CDR2-FR3-CDR3-FR4-C where

FR denotes a framework region amino acid sequence and CDR denotes a complementary determining region amino acid sequence.

In the present invention, the CDR1 consists of an amino acid sequence represented by RTIFNPNVMG (SEQ ID NO: 01).

In the present invention, the CDR2 consists of an amino acid sequence represented by DISLSGSTNYADSVKG (SEQ ID NO: 02).

In the present invention, the CDR3 consists of an amino acid sequence represented by NAISGAPGRY (SEQ ID NO: 03).

Desirably, the CDR1, the CDR2, and the CDR3 are represented by SEQ ID NO: 01, SEQ ID NO: 02, SEQ ID NO: 03 respectively. In this case, more desirably, the FR1, the FR2, the FR3, and the FR4 consist of amino acid sequences represented by QVQLVESGGGLVQAGGSLRLSCAAS (SEQ ID NO: 04), WYRQAPGKQRELVA (SEQ ID NO: 05), RFTISRDNAKNTMYLQMNSLKPEDTAVYYCNT (SEQ ID NO: 06), and WGQGAQVTVSS (SEQ ID NO: 07), respectively. In other words, it is desirable that the antibody according to the present invention consists of the following amino acid sequence.

```
                                    (SEQ ID NO: 08)
QVQLVESGGGLVQAGGSLRLSCAASRTIFNPNVMGWYRQAPGKQRELVAD

ISLSGSTNYADSVKGRFTISRDNAKNTMYLQMNSLKPEDTAVYYCNTNAI

SGAPGRYWGQGTQVTVSS
```

The antibody consisting of the amino acid sequence represented by SEQ ID NO: 08 does not exhibit antigen cross reactivity with regard to an influenza virus, such as an influenza virus type B, other than the influenza virus type A.

The antibody according to the present invention is employed in a detection device or in a detection method for detecting the intranuclear protein of an influenza virus type A. In this case, the antibody according to the present invention is used in a state where the antibody is bound to at least one selected from the group consisting of a solid support and a labeled substance.

As long as the solid support is a support insoluble in a solvent used for a reaction system of an antigen-antibody reaction, a shape and a material of the solid support is not limited. An example of the shape of the sol id support is a plate, a bead, a disk, a tube, a filter, and a film. An example of a material of the solid support is a polymer such as polyethylene terephthalate, cellulose acetate, polycarbonate, polystyrene, or polymethylmethacrylate, a metal such as gold, silver, or aluminum, or glass. A known method such as a physical adsorption method, a covalent binding method, an ion bonding method, or a cross-linking method is employed as a method for binding the antibody to the solid support.

For example, a labeled substance such as a fluorescent substance, a luminescent substance, a dye, and a radioactive substance is used. A known method such as a physical adsorption method, a covalent binding method, an ion bonding method, or a cross-linking method is employed as a method for binding the antibody to the labeled substance.

In the detection method in which the antibody according to the present invention is used, the composite including the antibody is brought into contact with an analyte. Then, detected is a change of a physical amount based on an antigen-antibody reaction of the intranuclear protein of the influenza virus type A contained in the analyte and the antibody included in the composite. An example of the physical amount is, for example, luminescence intensity, chromaticity, light transmission, turbidity, absorbance, or radiation dose. A known method such as an enzyme immunoassay method, an immunochromatography method, a latex agglutination method, a radioimmunoassay method, a fluorescence immunoassay method, or a surface plasmon resonance spectroscopy method is employed as an example of the detection method.

The detection device in which the antibody according to the present invention is employed includes a detector for detecting any one of the physical amount which may be changed on the basis of the antigen-antibody reaction. The detector is composed of a known device such as a photometer, a spectroscope, or a dosimeter.

EXAMPLES

Inventive Example 1

VHH antibodies capable of binding to an intranuclear protein included in an influenza virus type A H1N1 were prepared in accordance with the following procedures. Hereinafter, the intranuclear protein may be referred to as "NP".

(Immunization of Alpaca and Acquirement of Mononuclear)

In order to form a VHH antibody gene library, an alpaca was immunized using a recombinant intranuclear protein (SEQ ID NO: 24) derived from an Influenza virus type A H1N1 (A/Puerto Rico/8/34/Mount Sinai) as an antigen. The recombinant intranuclear protein was prepared using a Brevibacillus expression system by Higeta Shoyu Co., Ltd. The recombinant intranuclear protein was adjusted with an adjuvant before administrated to an alpaca.

The recombinant intranuclear protein used in the inventive example 1 is shown below.

```
                                    (SEQ ID NO: 24)
MASQGTKRSYEQMETDGERQNATEIRASVGKMIGGIGRFYIQMCTELKLS

DYEGRLIQNSLTIERMVLSAFDERRNKYLEEHPSAGKDPKKTGGPIYRRV

NGKWMRELILYDKEEIRRIWRQANNGDDATAGLTHMMIWHSNLNDATYQR

TRALVRTGMDPRMCSLMQGSTLPRRSGAAGAAVKGVGTMVMELVRMIKRG

INDRNFWRGENGRKTRIAYERMCNILKGKFQTAAQKAMMDQVRESRNPGN

AEFEDLTFLARSALILRGSVAHKSCLPACVYGPAVASGYDFEREGYSLVG

IDPFRLLQNSQVYSLIRPNENPAHKSQLVWMACHSAAFEDLRVLSFIKGT
```

-continued

KVLPRGKLSTRGVQIASNENMETMESSTLELRSRYWAIRTRSGGNTNQQR

ASAGQISIQPTFSVQRNLPFDRTTIMAAFNGNTEGRTSDMRTEIIRMMES

ARPEDVSFQGRGVFELSDEKAASPIVPSFDMSNEGSYFFGDNAEEYDN

Specifically, the recombinant intranuclear protein having a concentration of 100 micrograms/milliliter was administered to the alpaca. After one week, the recombinant HA protein having the same concentration was administered to the alpaca, again. In this way, the alpaca was immunized with the recombinant HA protein five times for five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subject to centrifugation under a temperature of 20 Celsius degrees at 1,000×g for one minute.

The blood extracted from the alpaca was treated with heparin. Then, an equivalent amount of phosphate buffered saline (hereinafter, referred to as "PBS") was added to the thus-treated blood to obtain a sample solution. Then, the sample solution was added to the lymphocyte separation tube to which the blood cell separation solution was added.

The lymphocyte separation tube was subject to centrifugation under a temperature of 20 Celsius degrees at 800×g for thirty minutes.

The fraction containing the mononuclear cells was collected. PBS having three times volume was added. The fraction was subject to centrifugation under a temperature of 20 Celsius degrees at 300×g for five minutes. The precipitate was suspended with PBS mildly. After the suspending, 10 microliters of the suspension was separated in order for the count of the number of the cell. The remaining suspension was subject to centrifugation under a temperature of 20 Celsius degrees at 300×g for five minutes.

A RNA storage solution (trade name: RNAlater) having a volume of 2 milliliters was added to the precipitate. Then, the solution was suspended mildly. The suspension was injected to two tubes each having a volume of 1.5 milliliters. Each tube included 1 milliliter of the suspension. The tube was stored under a temperature of −20 Celsius degrees. The suspension (5 microliters) separated for the count of the number of the cell was mixed with a Türk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of VHH antibody was formed in accordance with the following procedure. In the following procedure, RNase-free-grade reagents and instruments were used.

A total RNA isolation reagent (Trade name: TRIzol Regent, 1 milliliter) was added to the mononuclear cell fraction. The reagent was mixed mildly with the fraction, and left at rest at room temperature for five minutes. Chloroform (200 microliters) was added to the reagent, and the reagent was shaken strongly for fifteen seconds. The reagent was left at a room temperature for two-three minutes. The reagent was subject to centrifugation under a temperature of 4 Celsius degrees for 15 minutes at 12,000 or less ×g.

The supernatant was moved to a new tube. RNase-free water and chloroform (200 microliters, each) were added to the tube. In addition, 500 milliliters of isopropanol was added to the tube. The liquid included in the tube was stirred with a vortex mixer. The liquid was left at rest at room temperature for ten minutes. Then, the liquid was subject to centrifugation under a temperature of 4 Celsius degrees for fifteen minutes at 12,000 or less ×g. The supernatant was removed, and the precipitate was rinse with one milliliter of 75% ethanol. This solution was subject to centrifugation under a temperature of four Celsius degrees for five minutes at 7,500 or less ×g. The solution was dried to obtain total RNA. The obtained total RNA was solved in RNase-free water.

In order to obtain cDNA from the total RNA, a kit including a reverse transcriptase was employed. The kit was available from Takara Bio Inc., as a trade name of PrimeScript II 1st strand cDNA Synthesis Kit. The Random 6 mer and Oligo dT primer included in the kit were used as primers. The cDNA was obtained in accordance with the standard protocol attached in the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10x buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subject to the following PCR method.

First, the mixture solution was heated at temperature of 95 Celsius degrees for two minutes.

Then, the temperature of the mixture solution was varied in accordance with the following cycle.

Ninety six Celsius degrees for thirty seconds,

Fifty two Celsius degrees for thirty seconds, and

Sixty eight Celsius degrees for forty seconds

This cycle was repeated thirty times.

Finally, the mixture solution was heated at temperature of sixty eight Celsius degrees for four minutes and stored at temperature of four Celsius degrees.

The following primers were used in the present PCR method.

Primer 1:
(SEQ ID NO: 09)
5'-GGTGGTCCTGGCTGC-3'

Primer 2:
(SEQ ID NO: 10)
5'-ctgctcctcgcGGCCCAGCCGGCCatggcTSAGKTGCAGC
TCGTGGAGTC-3'

Primer 3:
(SEQ ID NO: 11)
5'-TGGGGTCTTCGCTGTGGTGCG-3'

Primer 4:
(SEQ ID NO: 12)
5'-TTGTGGTTTTGGTGTCTTGGG-3'

Primer 5:
(SEQ ID NO: 13)
5'-tttgCtctGCGGCCGCagaGGCCgTGGGGTCTTCGCTGTG
GTGCG-3'

Primer 6:
(SEQ ID NO: 14)
5'-tttgCtctGCGGCCGCagaGGCCgaTTGTGGTTTTGGTGT
CTTGGG-3'

(Reference literature: Biomed Environ Sci., 2012; 27(2): 118-121)

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4.

In the third PCR assay, a primer set E composed of the gene amplified with the primer set C, Primer 2, and Primer 5, and a primer set F composed of the gene amplified with the primer set D, Primer 2, and Primer 6.

In this way, the gene library of the VHH antibody was formed. In other words, the gene library of the VHH antibody included the genes amplified with the primer sets E and F.

(Formation of Phage Library)

Next, a phase library was formed from the gene library of the VHH antibody in accordance of the following procedures.

Figure 1B:
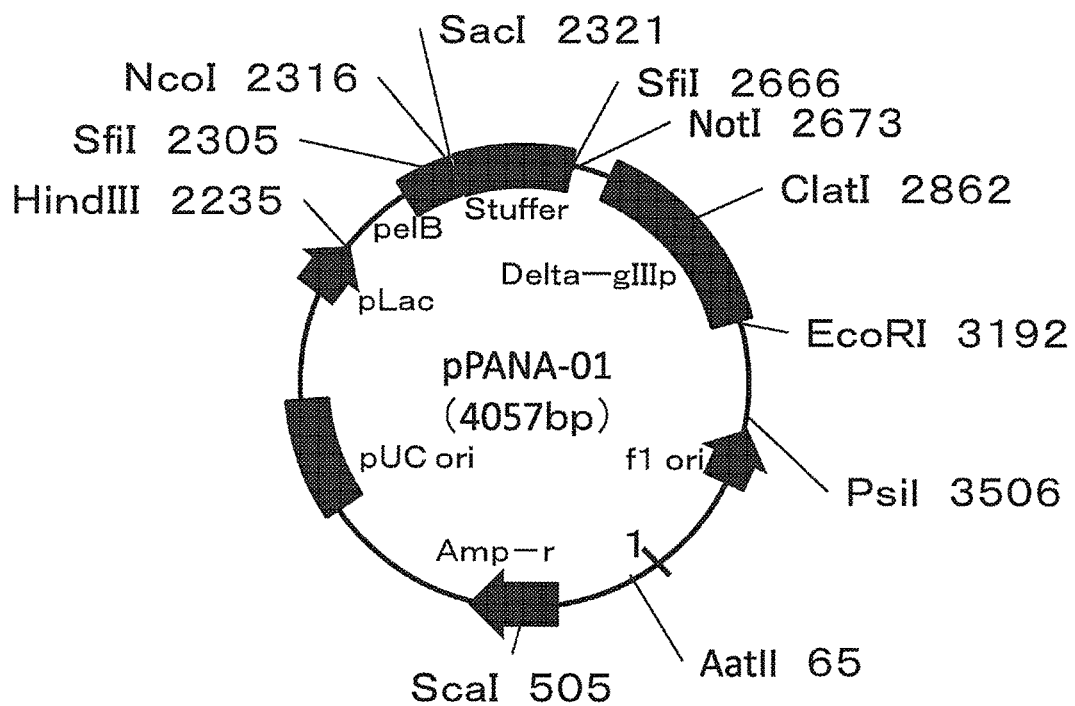
FIG. 1B shows the detail of the vector map shown in FIG. 1A.

A plasmid Vector 1 (4057 bp, see FIG. 1A) derived from a commercially available plasmid pUC119 (for example, available from Takara Bio. Inc.) was treated with a restriction enzyme SfiI. The restriction enzyme site SfiI(a) consists of the gene sequence represented by GGCCCAGCCGGCC (SEQ ID NO: 15). The restriction enzyme site SfiI(b) consists of the gene sequence represented by GGCCTCT-GCGGCC (SEQ ID NO: 16). FIG. 1B shows a detail vector map of the plasmid Vector 1.

The plasmid Vector 1 consists of the following gene sequence.

(SEQ ID NO: 17)
gacgaaagggcctcgtgatacgcctatttttataggttaatgtcatgata ataatggtttcttagacgtcaggtggcacttttcggggaaatgtgcgcgg aaccctatttgtttatttttctaaatacattcaaatatgtatccgctca tgagacaataaccctgataaatgcttcaataatattgaaaaaggaagagt atgagtattcaacatttccgtgtcgcccttattccctttttttgcggcatt ttgccttcctgttttttgctcacccagaaacgctggtgaaagtaaaagatg ctgaagatcagttgggtgcacgagtgggttacatcgaactggatctcaac agcggtaagatccttgagagttttcgccccgaagaacgttttccaatgat gagcacttttaaagttctgctatgtggcgcggtattatcccgtattgacg ccgggcaagagcaactcggtcgccgcatacactattctcagaatgacttg gttgagtactcaccagtcacagaaaagcatcttacggatggcatgacagt aagagaattatgcagtgctgccataaccatgagtgataacactgcggcca acttacttctgacaacgatcggaggaccgaaggagctaaccgcttttttg cacaacatgggggatcatgtaactcgccttgatcgttgggaaccggagct gaatgaagccataccaaacgacgagcgtgacaccacgatgcctgtagcaa tggcaacaacgttgcgcaaactattaactggcgaactacttactctagct tcccggcaacaattaatagactggatggaggcggataaagttgcaggacc acttctgcgctcggcccttccggctggctggtttattgctgataaatctg gagccggtgagcgtgggtctcgcggtatcattgcagcactggggccagat ggtaagccctcccgtatcgtagttatctacacgacggggagtcaggcaac tatggatgaacgaaatagacagatcgctgagataggtgcctcactgatta agcattggtaactgtcagaccaagtttactcatatatactttagattgat ttaaaacttcatttttaatttaaaaggatctaggtgaagatcctttttga taatctcatgaccaaaatcccttaacgtgagttttcgttccactgagcgt cagaccccgtagaaaagatcaaaggatcttcttgagatcctttttttctg cgcgtaatctgctgcttgcaaacaaaaaaaccaccgctaccagcggtggt ttgtttgccggatcaagagctaccaactcttttttccgaaggtaactggct tcagcagagcgcagataccaaatactgtccttctagtgtagccgtagtta ggccaccacttcaagaactctgtagcaccgcctacatacctcgctctgct aatcctgttaccagtggctgctgccagtggcgataagtcgtgtcttaccg ggttggactcaagacgatagttaccggataaggcgcagcggtcgggctga acggggggttcgtgcacacagcccagcttggagcgaacgacctacaccga actgagatacctacagcgtgagctatgagaaagcgccacgcttcccgaag ggagaaaggcggacaggtatccggtaagcggcagggtcggaacaggagag cgcacgagggagcttccaggggggaaacgcctggtatctttatagtcctgt cgggtttcgccacctctgacttgagcgtcgatttttgtgatgctcgtcag gggggcggagcctatggaaaaacgccagcaacgcggcctttttacggttc ctggccttttgctggccttttgctcacatgttctttcctgcgttatcccc tgattctgtggataaccgtattaccgcctttgagtgagctgataccgctc gccgcagccgaacgaccgagcgcagcgagtcagtgagcgaggaagcggaa gagcgcccaatacgcaaaccgcctctccccgcgcgttggccgattcatta atgcagctggcacgacaggtttcccgactggaaagcgggcagtgagcgca acgcaattaatgtgagttagctcactcattaggcaccccaggctttacac tttatgcttccggctcgtatgttgtgtggaattgtgagcggataacaatt tcacacaggaaacagctatgaccatgattacgccAAGCTTCGAAGGAGAC AGTCATAatgaaatacctgctgccgaccgctgctgctggtctgctgctcc tcgcGGCCCAGCCGGCCatggagcTCAAGATGACACAGACTACATCCTCC

CTGTCAGCCTCTCTGGGAGACAGAGTCACCATCAGTTGCAGGGCAAGTCA

GGACATTAGCGATTATTTAAACTGGTATCAGCAGAAACCAGATGGAACTG

TTAAACTCCTGATCTATTACACATCAAGTTTACACTCAGGAGTCCCATCA

AGGTTCAGTGGCGGTGGGTCTGGAACAGATTATTCTCTCACCATTAGCAA

CCTGGAGCAAGAAGATATTGCCACTTACTTTTGCCAACAGGGTAATACGC

TTCCGTGGACGTTTGGTGGAGGCACCAAGCTGGAAATCAAACGGGCTGAT

GCTGCACCAACTGtaGGCCtctGCGGCCGCagaGcaaaaactcatctcag aagaggatctgaatggggccgcaTAGggttccggtgattttgattatgaa aagatggcaaacgctaataaggggctatgaccgaaaatgccgatgaaaa -continued

```
cgcgctacagtctgacgctaaaggcaaacttgattctgtcgctactgatt acggtgctgctatcgatggtttcattggtgacgtttccggccttgctaat ggtaatggtgctactggtgattttgctggctctaattcccaaatggctca agtcggtgacggtgataattcacctttaatgaataatttccgtcaatatt taccttccctccctcaatcggttgaatgtcgccttttgtctttagcgct ggtaaaccatatgaattttctattgattgtgacaaaataaacttattccg tggtgtctttgcgtttcttttatatgttgccacctttatgtatgtatttt ctacgtttgctaacatactgcgtaataaggagtctTAATAAgaattcact ggccgtcgttttacaacgtcgtgactgggaaaaccctggcgttacccaac ttaatcgccttgcagcacatccccctttcgccagctggcgtaatagcgaa gaggcccgcaccgatcgcccttcccaacagttgcgcagcctgaatggcga atggcgcctgatgcggtattttctccttacgcatctgtgcggtatttcac accgCATATGaAAATTGTAAgcgttaatattttgttaaaattcgcgttaa attttttgttaaatcagctcattttttaaccaataggccgaaatcggcaaa atcccttataaatcaaaagaatagaccgagatagggttgagtgttgttcc agtttggaacaagagtccactattaaagaacgtggactccaacgtcaaag ggcgaaaaaccgtctatcagggcgatggcccactacgtgaaccatcaccc taatcaagttttttggggtcgaggtgccgtaaagcactaaatcggaaccc taaagggagccccgatttagagcttgacggggaaagccggcgaacgtgg cgagaaaggaagggaagaaagcgaaaggagcgggcgctagggcgctggca agtgtagcggtcacgctgcgcgtaaccaccacacccgccgcgcttaatgc gccgctacaGGGCGCGTcccatATGgtgcactctcagtacaatctgctct gatgccgcatagttaagccagccccgacacccgccaacacccgctgacgc gccctgacgggcttgtctgctcccggcatccgcttacagacaagctgtga ccgtctccgggagctgcatgtgtcagaggttttcaccgtcatcaccgaaa cgcgcga
```

Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected to the mixture solution. The mixture solution was left at rest at a temperature of 16 Celsius degrees for two hours. In this way, each of the VHH antibody gene fragments was ligated into the plasmid Vector 1.

Coli bacteria (available from Takara Bio. Inc., trade name: HST02) were transfected with the thus-ligated plasmid Vector 1.

Then, the coli bacteria were incubated for fifteen hours on a 2YT plate culture medium containing ampicillin at a concentration of 100 micrograms/milliliter. In this way, obtained was a library of phases each of which displays a protein obtained from the gene fragment included in the gene library of the VHH antibody.

After the incubation, a concentration of the library was calculated by counting the number of single colonies formed on the 2YT plate culture medium. As a result, the library of the phases had a concentration of $5 \times 10^7$/milliliter.

(Biopanning)

VHH antibodies capable of specifically binding to the intranuclear protein were obtained from the phage library in accordance with the following procedures.

In order to extract the clones each capable of the antigen from among the phases which expressed the VHH antibody, biopanning was conducted twice.

Coli bacteria (HST02) to which the VHH antibody gene fragment included in the gene library of the VHH antibody was introduced were incubated at temperature of 30 Celsius degrees in the 2YT AG culture medium containing 100 micrograms/milliliter of ampicillin and 1% glucose in such a manner that a value $OD_{600}$ indicating absorbance reached 1.0. The 2YT AG culture has a volume of 100 milliliters. In this way, the Coli bacteria were proliferated.

Helper phages (available from Invitrogen company, trade name: M13K07) were added to the coli bacteria culture medium in such a manner that the multiplicity of infection was approximately twenty.

Then, the culture medium was warmed for about thirty minutes at temperature of 37 Celsius degrees. Then, the culture medium was subject to centrifugation at rotation speed of 4000 rpm for ten minutes to collect the coli bacteria. The coli bacteria was incubated overnight at temperature of 30 Celsius degrees in a 2YTAK culture medium containing 100 micrograms/milliliter of ampicillin and 1% 50 micrograms/milliliter of kanamycin, while subjected to centrifugation at 213 rpm.

The incubation liquid (100 milliliters) containing the thus-incubated coli bacteria were injected to two centrifugation tubes (volume: 50 milliliters, each). The two centrifugation tubes were subject to centrifugation for ten minutes at rotation speed of 4,000 rpm. Then, the supernatants (20 milliliters, each) were collected.

The supernatants (40 milliliters) were added to a 20% polyethylene glycol solution (10 milliliters) containing NaCl (2.5M). Then, the mixture solution was mixed upward down. Subsequently, the mixture solution was cooled on an ice for approximately one hour. The mixture was subject to centrifugation for ten minutes at rotation speed of 4,000 rpm. Then, the supernatant was removed. PBS containing 10% glycerol was injected toward the precipitate. Finally, the precipitate was loosened and dissolved. In this way, a library of phases each of which displays the VHH antibody was obtained.

(Screening of the VHH Antibody Capable of Specifically Binding to NP)

(A) Immobilization of NP Antigen

NP was mixed with PBS to prepare an NP solution. The concentration of NP was 2 micrograms/milliliter. The NP solution (2 milliliters) was injected into an immunotube (available from NUNC Co. Ltd.). The NP solution was left at rest in the immunotube for one hour. In this way, NP was immobilized in the immunotube.

Then, the inside of the immunotube was washed three times with PBS.

The inside of the immunotube was filled with PBS which contained 3% skim milk (available from Wako Pure Chemical Industries, Ltd.). In this way, NP was blocked as an antigen in the immunotube.

The immunotube was left at rest at room temperature for one hour. Subsequently, the inside of the immunotube was washed three times with PBS.

(B) Panning

The library of the phages each of which displays the VHH antibody (Concentration: approximately 10E+11/milliliter) was mixed with 3 milliliters of PBS containing 3% skim milk to prepare a mixture solution. The mixture solution was injected into the immunotube in which the NP antigen was immobilized.

The immunotube was provided with a lid formed of a parafilm. Then, the immunotube was rotated upward down in a rotator for ten minutes.

The immunotube was left at rest at room temperature for one hour.

The inside of the immunotube was washed ten times with PBS containing 0.05% tween 20. Hereinafter, such a PBS is referred to as "PBST".

The inside of the immunotube was filled with PBST. Subsequently, the immunotube was left at rest for ten minutes. Then, the inside of the immunotube was washed ten times with PBST.

In order to extract phases each of which displays the VHH antibody bound to the NP antigen, 100 mM trimethylamine solution (1 milliliters) was injected to the immunotube.

The immunotube was provided with a lid formed of a parafilm. Then, the immunotube was rotated upward down in a rotator for ten minutes.

In order to neutralize the solution, the solution was moved to a tube containing 1 mL of 0.5M Tris/HCl (pH: 6.8). Again, the extraction of the phase was repeated using a 100 mM trimethylamine solution (1 milliliter). In this way, 3 mL of the extraction liquid was obtained.

The extraction liquid (1 mL) was mixed with 9 mL of *coli* bacteria HST02. The mixture solution was left at rest for one hour at temperature of 30 Celsius degrees.

In order to count the number of colonies, 10 microliters of the mixture solution containing the *coli* bacteria HST02 was distributed onto a small plate including a 2TYA culture medium (10 milliliters/plate).

The rest of the mixture solution was subject to centrifugation. The supernatant was removed, and the precipitate was distributed onto a large plate including a 2TYA culture medium (40 milliliters/plate). These two plates were left at rest overnight at temperature of 30 Celsius degrees. In this way, first panning was conducted.

Second panning was conducted identically to the procedure of the first panning. In other words, the panning was repeated. In this way, the monoclonal phases on which the VHH antibody was displayed were purified.

After the second panning, a colony of the *coli* bacteria was picked up with a toothpick. The picked-up one colony was put onto one well of 96-flat-bottom plate. This was repeated. One well contained 200 microliter of a 2YTAG culture medium.

The solutions included in the wells were stirred at a rotation speed of 213 rpm at temperature of 30 Celsius degrees.

The solution (50 microliters) containing grown *coli* bacteria was collected. The collected solution was mixed with 50 microliters of a 2YTA culture medium included in a plate. The 2YTA culture medium contained helper phases such that the multiplicity of infection (i.e., MOI) was set to be 20. The solution was left at rest at temperature of 37 Celsius degrees for forty minutes.

The plate including the 2YTA culture medium was subject to centrifugation at 1,800 rpm for twenty minutes. The supernatant was removed. The precipitate contained the coil bacteria. The precipitate was mixed with 200 microliters of a 2YTAK culture medium. The mixture solution was left at rest overnight at temperature of 30 Celsius degrees.

The mixture solution was subject to centrifugation at 1800 rpm for twenty minutes. The supernatant containing the *coli* bacteria was collected.

(C) Qualitative Evaluation of Phase-Displayed VHH Antibody and Antigen by ELISA

An intranuclear protein solution having a concentration of 2 micrograms/milliliter was injected as an antigen into each of the wells of 96-well plate (available from Thermo scientific company, trade name: maxisorp). The volume of the intranuclear protein solution in each well was 50 microliters. The 96-well plate was left at rest at room temperature for one hour. In this way, the NP antigen was immobilized in each well.

Each of the wells was washed with PBS three times. Then, PBS containing 3% skim milk (available from Wako Pure Chemical Industries, Ltd.) was injected into each well (200 microliters/well). The 96-well plate was left at rest at room temperature for one hour. In this way, the intranuclear protein was blocked in each well. Subsequently, each well was washed three times with PBS.

(The monoclonal phases each of which displays the VHH antibody were injected into each well (50 microliters/well). Then, the 96-well plate was left at rest for one hour. In this way, the phases reacted with the NP antigen.

Each well was washed three times with PBST. Then, anti-M13 antibody (available from ABCAM company, trade name; ab50370, 10,000-fold dilution) was injected into each well (50 microliters/well). Then, each well was washed three times with PBST.

A color-producting agent (available from Thermo Scientific, trade name: 1-step ultra TMB-ELISA) was injected into each well (50 microliters/well). The 96-well plate was left at rest for two minutes to cause the color-producting agent to react with the antibody.

A sulfuric acid aqueous solution (normal, i.e., 1N) was injected into each well at a concentration of 50 microliters/well to cease the reaction.

The absorbance of the solution at a wavelength of 450 nanometers was measured.

Six wells each having good absorbance measurement result were selected. The DNA sequences included in the phases contained in the selected six wells were analyzed by Greiner Company. The analysis results of the DNA sequences will be described below. The following one DNA sequences were found.

(SEQ ID NO: 18)
GCTCAGGTGCAGCTCGTGGAGTCTGGGGGAGGCTTGGTGCAGGCTGGGGG

GTCTCTGAGACTCTCCTGTGCAGCCTCTCGAACCATCTTCAATCCGAATG

TCATGGGCTGGTACCGCCAGGCTCCAGGGAAGCAGCGCGAGTTGGTCGCA

GATATTAGTTTAAGTGGCAGCACAAACTATGCAGACTCCGTGAAGGGCCG

ATTCACGATCTCCAGAGACAACGCCAAGAACACGATGTATCTGCAAATGA

ACAGCCTGAAGCCTGAGGATACAGCCGTCTATTATTGTAATACTAATGCG

ATCAGCGGTGCGCCCGGAAGGTACTGGGGCCAGGGGACCCAGGTCACCGT

CTCCTCA

The protein synthesized from the DNA sequence represented by SEQ ID NO: 18 consists of the following amino acid sequence.

(SEQ ID NO: 08)
QVQLVESGGGLVQAGGSLRLSCAASRTIFNPNVMGWYRQAPGKQRELVAD

ISLSGSTNYADSVKGRFTISRDNAKNTMYLQMNSLKPEDTAVYYCNTNAI

SGAPGRYWGQGTQVTVSS (Expression of Anti-NP VHH Antibody)

Figure 2:
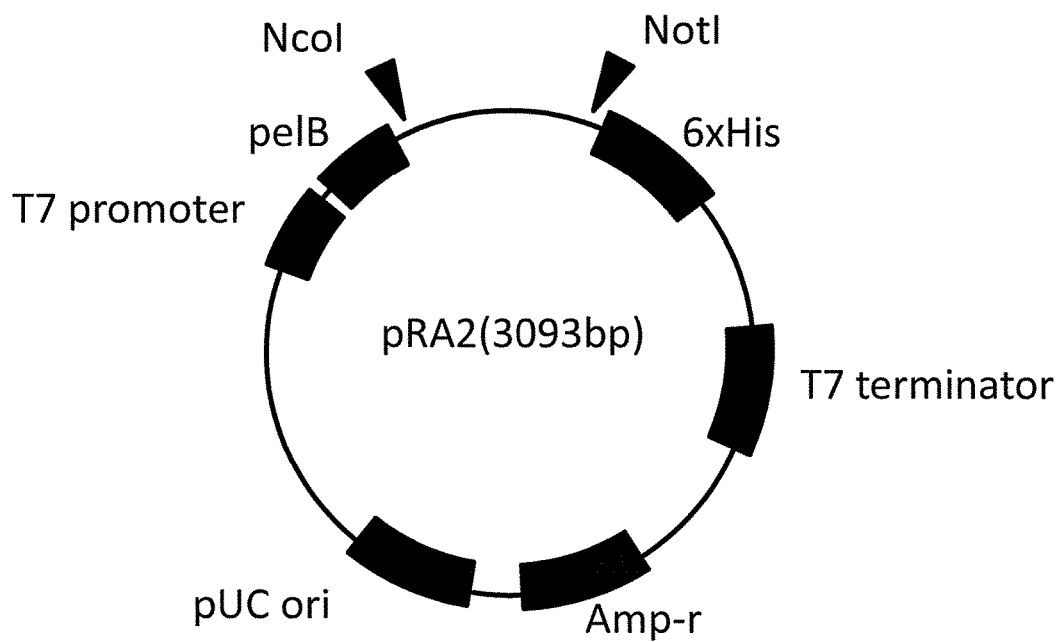
FIG. 2 is a vector map used to express the VHH antibody.
Figure 3A:
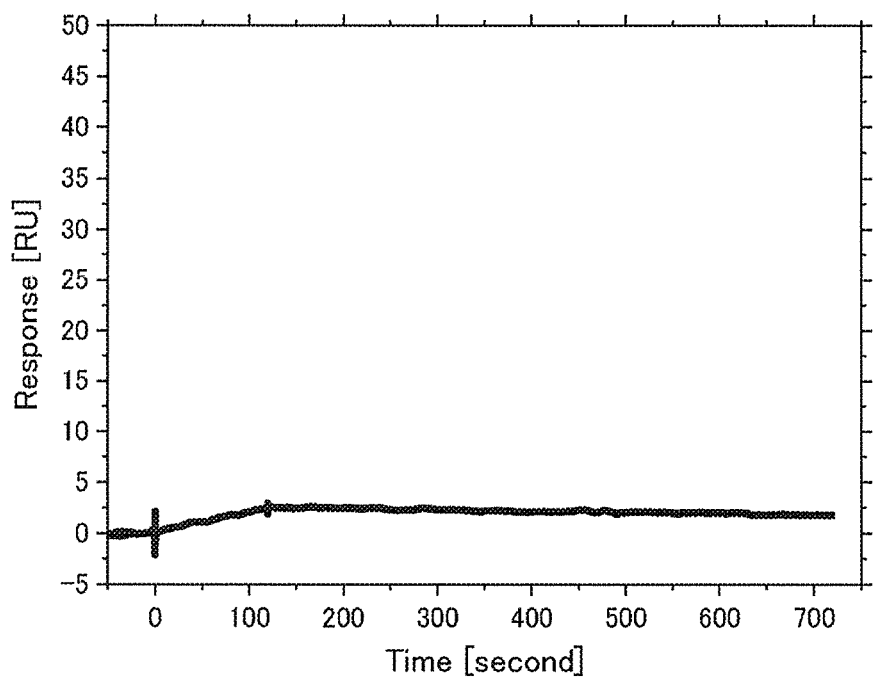
FIG. 3A is a graph showing a SPR evaluation result of the binding ability of the VHH antibody (concentration: 0.195 nM) consisting of the amino acid sequence represented by SEQ ID NO: 08 to the recombinant intranuclear protein.
Figure 3B:
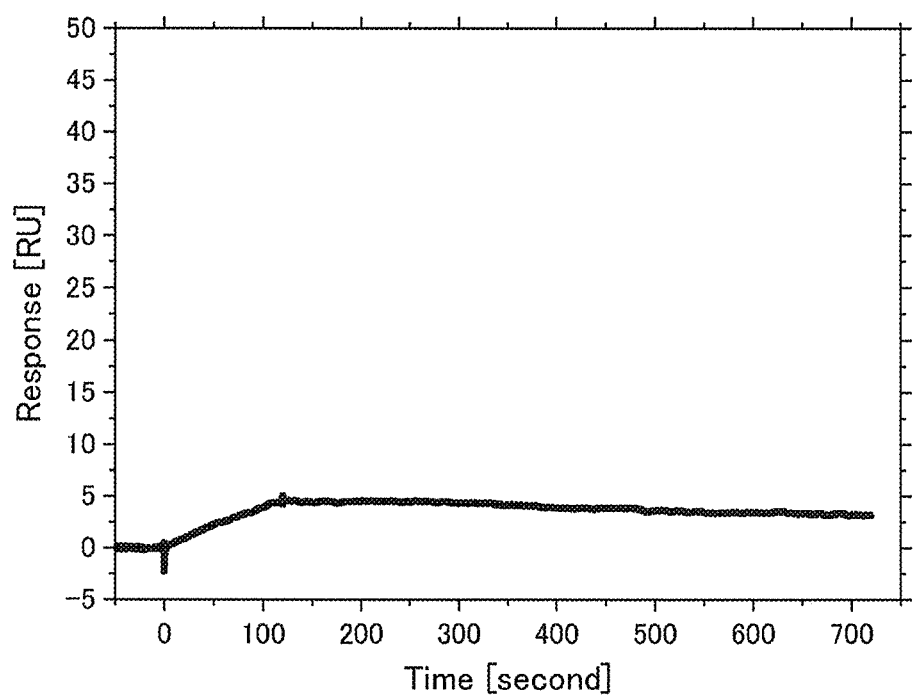
FIG. 3B is a graph showing a SPR evaluation result of the binding ability of the VHH antibody (concentration: 0.39 nM) consisting of the amino acid sequence represented by SEQ ID NO: 08 to the recombinant intranuclear protein.
Figure 3C:
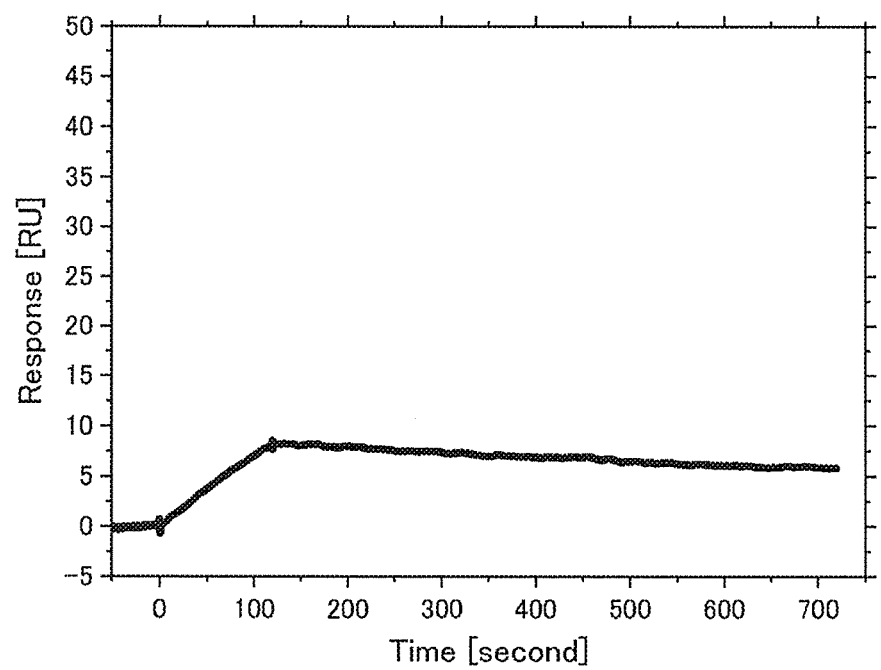
FIG. 3C is a graph showing a SPR evaluation result of the binding ability of the VHH antibody (concentration: 0.78 nM) consisting of the amino acid sequence represented by SEQ ID NO: 08 to the recombinant intranuclear protein.
Figure 3D:
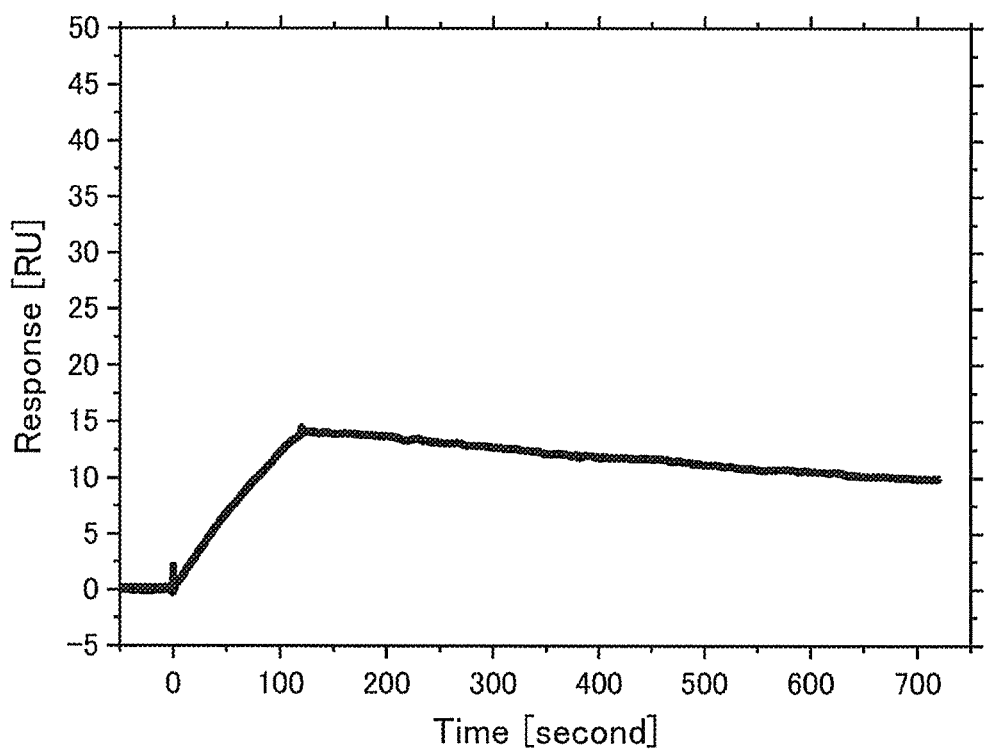
FIG. 3D is a graph showing a SPR evaluation result of the binding ability of the VHH antibody (concentration: 1.56 nM) consisting of the amino acid sequence represented by SEQ ID NO: 08 to the recombinant intranuclear protein.
Figure 3E:
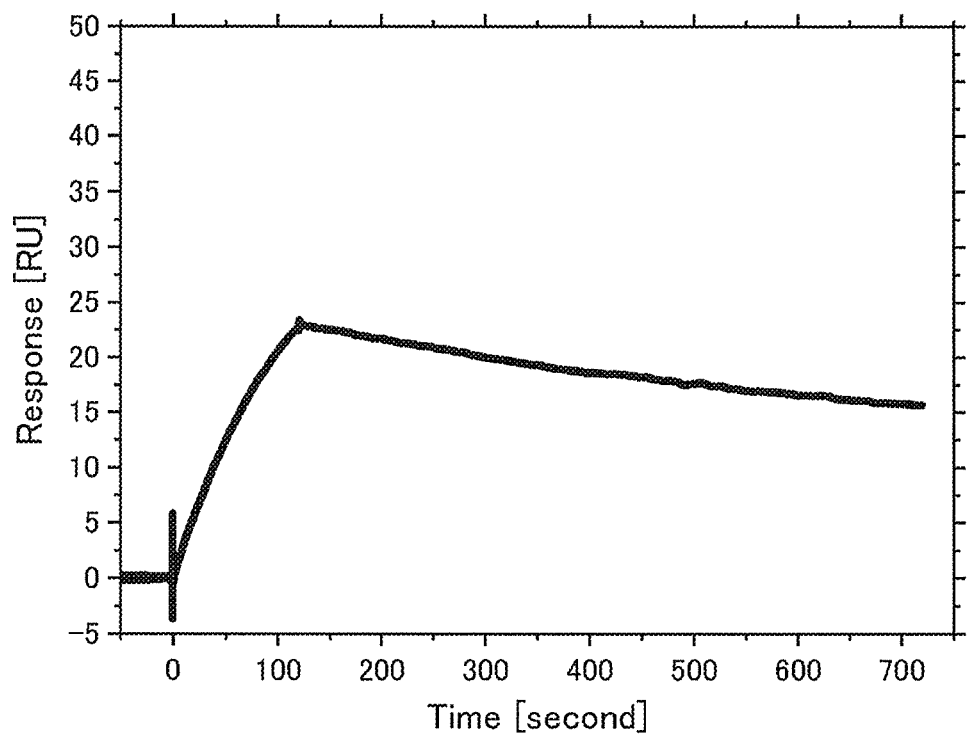
FIG. 3E is a graph showing a SPR evaluation result of the binding ability of the VHH antibody (concentration: 3.125 nM) consisting of the amino acid sequence represented by SEQ ID NO: 08 to the recombinant intranuclear protein.
Figure 3F:
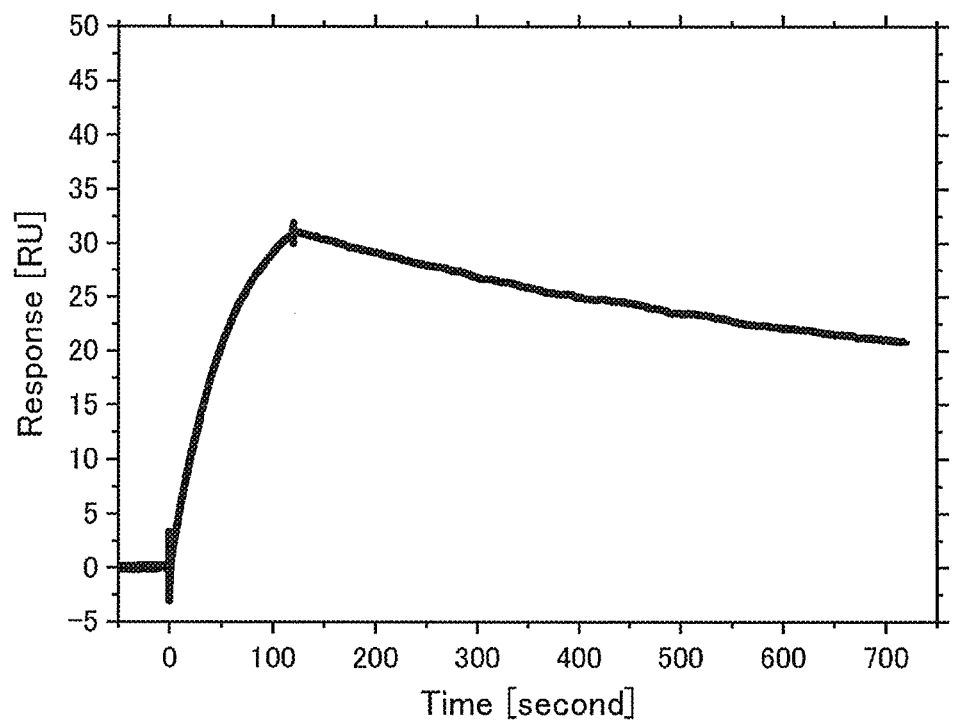
FIG. 3F is a graph showing a SPR evaluation result of the binding ability of the VHH antibody (concentration: 6.25 nM) consisting of the amino acid sequence represented by SEQ ID NO: 08 to the recombinant intranuclear protein.
Figure 3G:
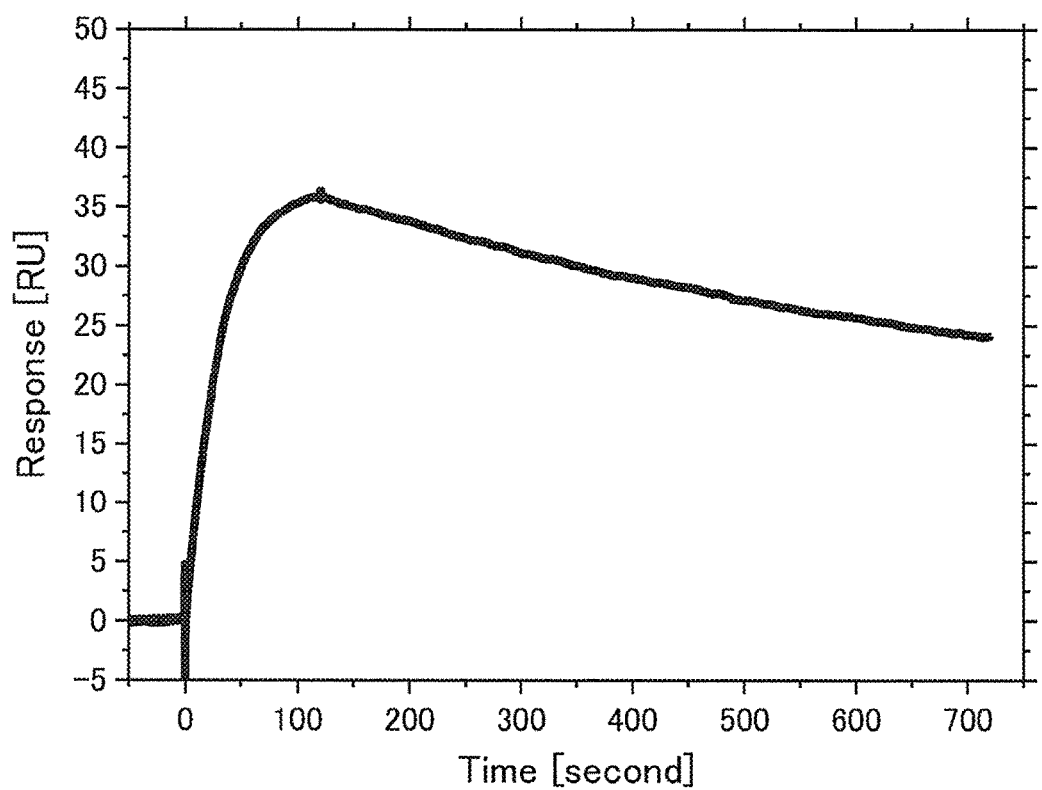
FIG. 3G is a graph showing a SPR evaluation result of the binding ability of the VHH antibody (concentration: 12.5 nM) consisting of the amino acid sequence represented by SEQ ID NO: 08 to the recombinant intranuclear protein.
Figure 4A:
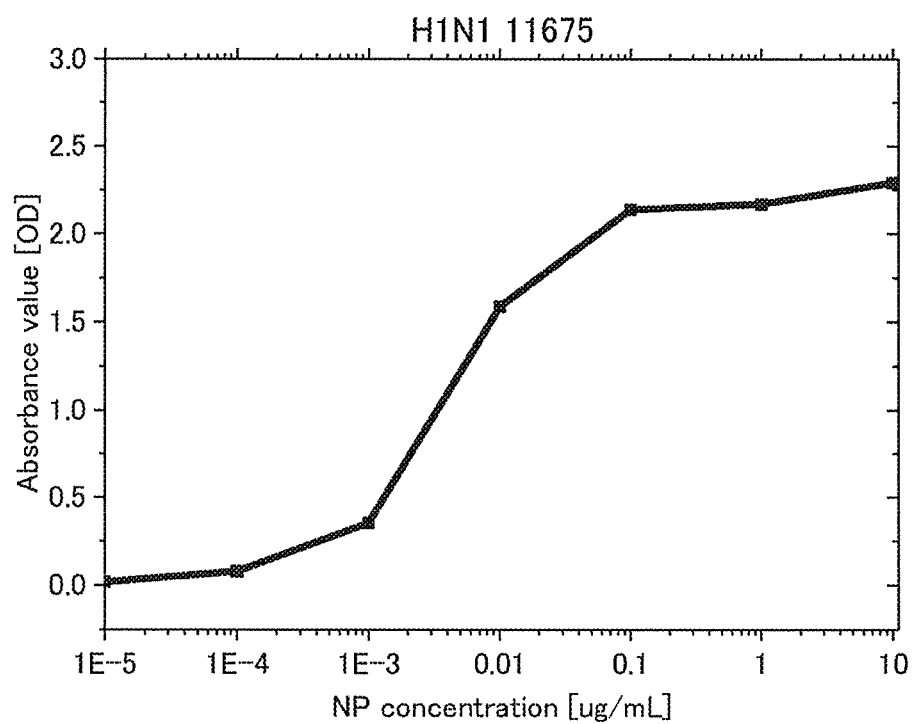
FIG. 4A is a graph showing the measurement result of the cross reactivity of the VHH antibody consisting of the amino acid sequence represented by SEQ ID NO: 08 with regard to the influenza virus type A H1N1 11675.
Figure 4B:
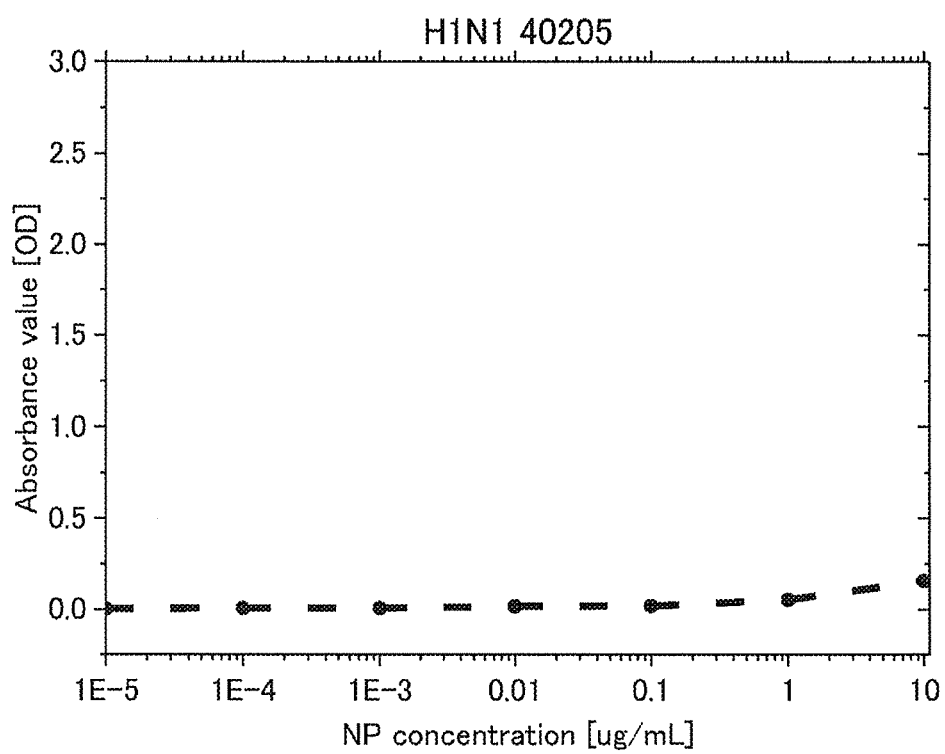
FIG. 4B is a graph showing the measurement result of the cross reactivity of the VHH antibody consisting of the amino acid sequence represented by SEQ ID NO: 08 with regard to the influenza virus type A H1N1 40205.
Figure 4C:
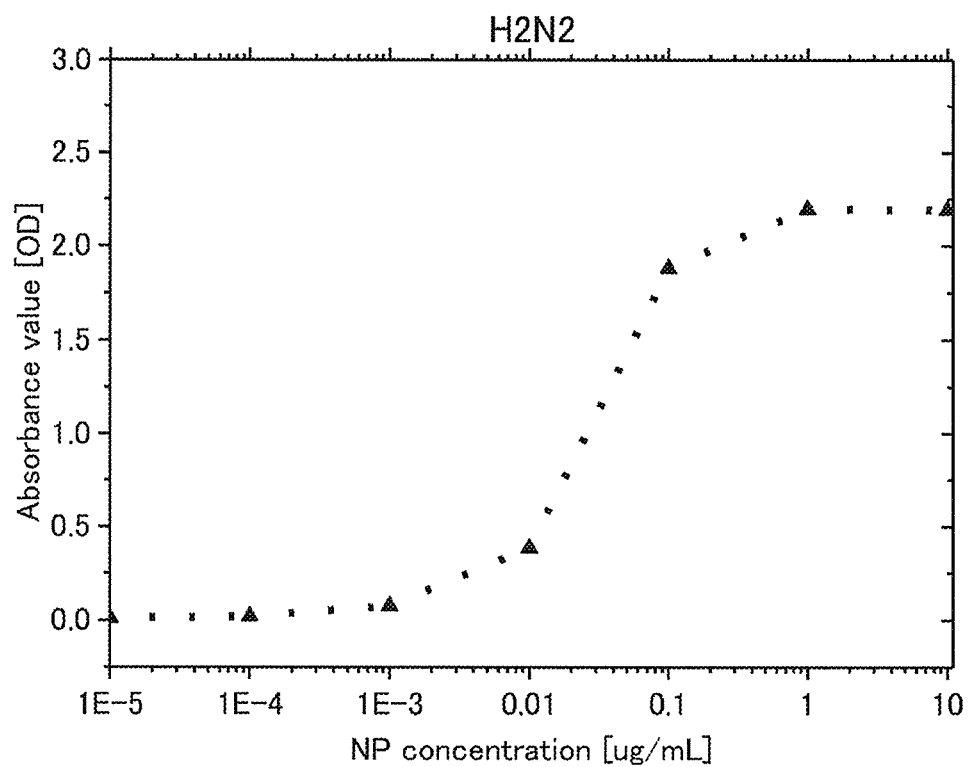
FIG. 4C is a graph showing the measurement result of the cross reactivity of the VHH antibody consisting of the amino acid sequence represented by SEQ ID NO: 08 with regard to the influenza virus type A H2N2.
Figure 4D:
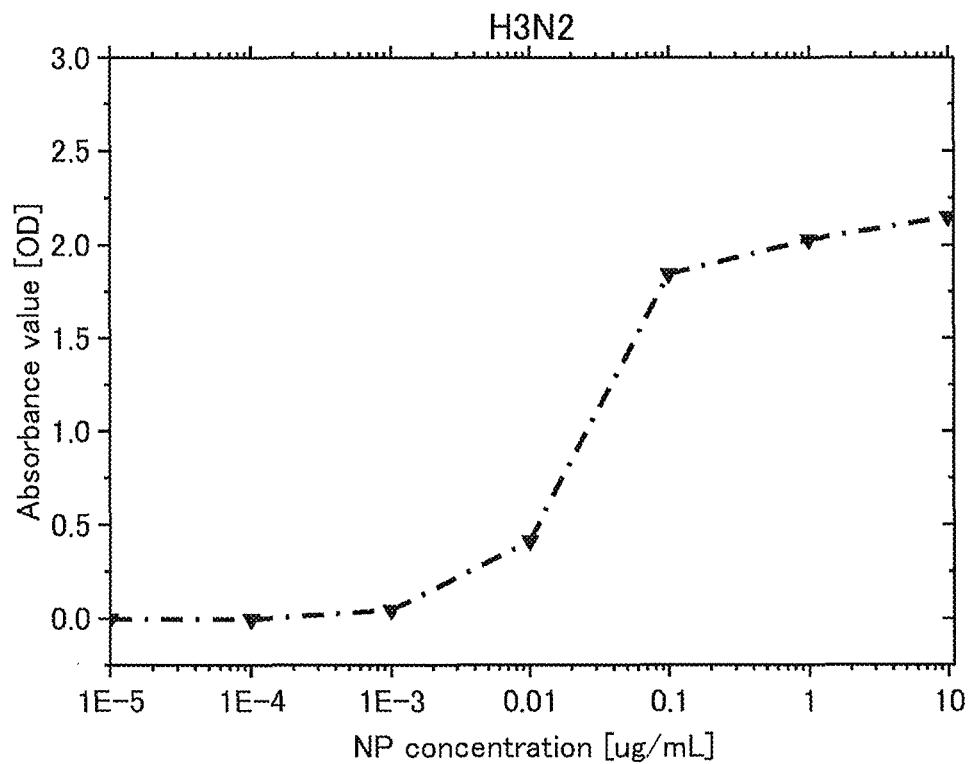
FIG. 4D is a graph showing the measurement result of the cross reactivity of the VHH antibody consisting of the amino acid sequence represented by SEQ ID NO: 08 with regard to the influenza virus type A H3N2.
Figure 4E:
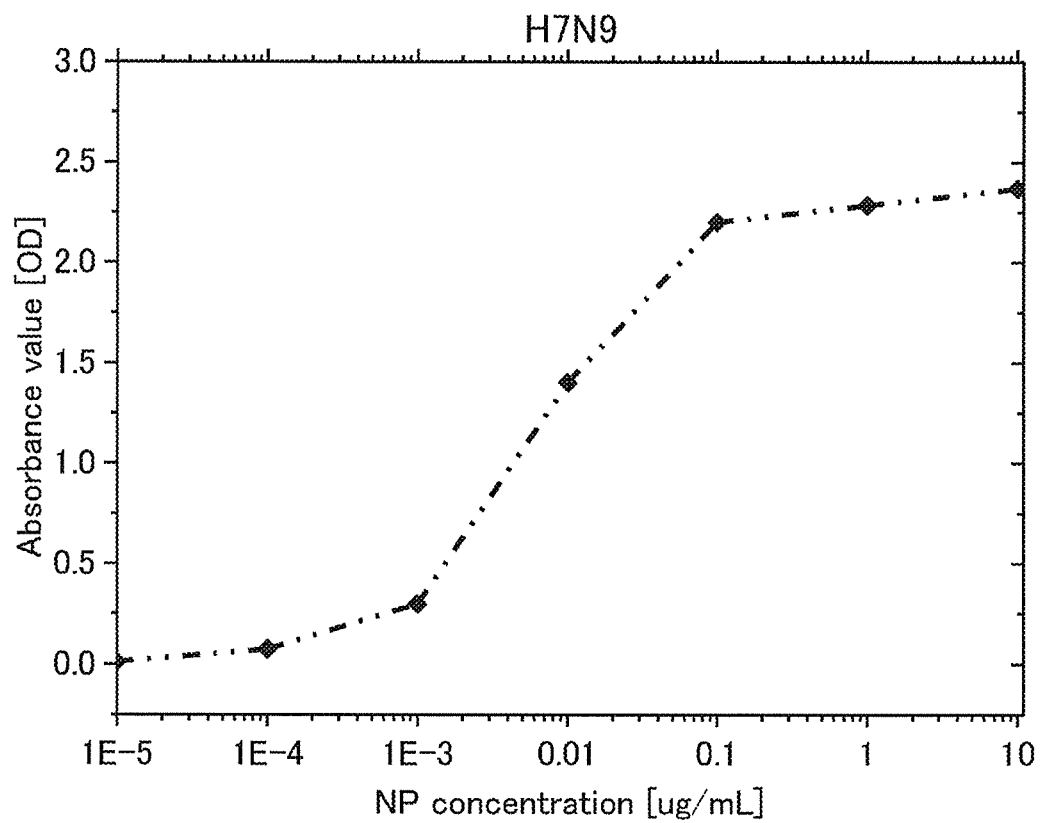
FIG. 4E is a graph showing the measurement result of the cross reactivity of the VHH antibody consisting of the amino acid sequence represented by SEQ ID NO: 08 with regard to the influenza virus type A H7N9.
Figure 4F:
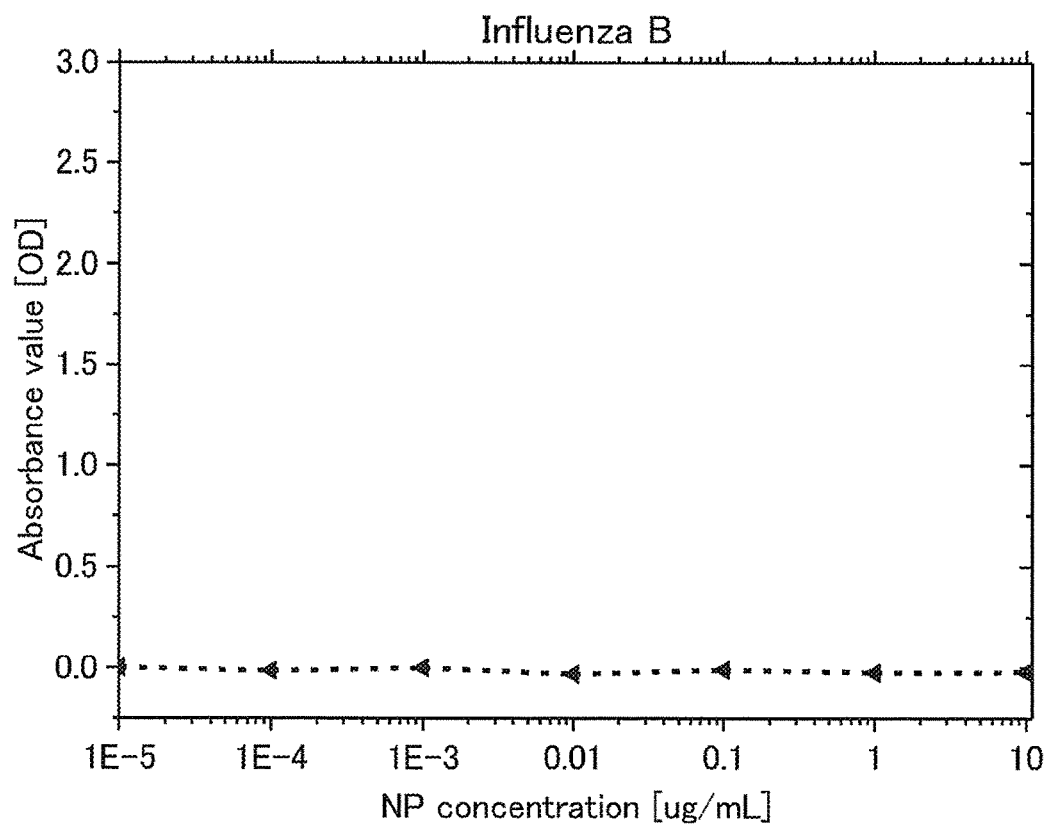
FIG. 4F is a graph showing the measurement result of the cross reactivity of the VHH antibody consisting of the amino acid sequence represented by SEQ ID NO: 08 with regard to the influenza virus type B.

A vector pRA2(+) was purchased from Merck Millipore Company as an expression vector (See FIG. 2). Using In-Fusion HD Cloning Kit (available from Takara Bio Inc.), the VHH sequence was ligated into a vector pRA2(+). Hereinafter, the ligation process will be described below in more detail.

First, a VHH antibody gene fragment was amplified by the PCR method using the following two primers (SEQ ID NO: 17 and SEQ ID NO: 18) from the plasmid Vector 1 in which the VHH antibody gene fragment included in the gene library of the VHH antibody was ligated. In this way, the following one DNA (SEQ ID NO: 19) including a gene sequence coding for the amino acid sequence represented by the SEQ ID NO: 08 was obtained.

Primer 1:
(SEQ ID NO: 19)
5'-CAGCCGGCCATGGCTGCTCAGGTGCAGCTCGTGGAGTC-3'

Primer 2:
(SEQ ID NO: 20)
5'-ATGGTGGCGGCCGCGTGAGGAGACGGTGACCTGGGTCC-3'

(SEQ ID NO: 21)
5'-CAGCCGGCCATGGCTGCTCAGGTGCAGCTCGTGGAGTCTGGGGGAGG

CTTGGTGCAGGCTGGGGGGTCTCTGAGACTCTCCTGTGCAGCCTCTCGAA

CCATCTTCAATCCGAATGTCATGGGCTGGTACCGCCAGGCTCCAGGGAAG

CAGCGCGAGTTGGTCGCAGATATTAGTTTAAGTGGCAGCACAAACTATGC

AGACTCCGTGAAGGGCCGATTCACGATCTCCAGAGACAACGCCAAGAACA

CGATGTATCTGCAAATGAACAGCCTGAAGCCTGAGGATACAGCCGTCTAT

TATTGTAATACTAATGCGATCAGCGGTGCGCCCGGAAGGTACTGGGGCCA

GGGGACCCAGGTCACCGTCTCCTCACGCGGCCGCCACCAT-3'

On the other hand, a part of the base sequence included in the vector pRA2 was amplified by a PCR method using the following two primers (SEQ ID NO: 22 and SEQ ID NO: 23). In this way, a DNA (SEQ ID NO: 25) was obtained.

Primer 1:
(SEQ ID NO: 22)
5'-CGCGGCCGCCACCATCATCACCACCATTAATAG-3'

Primer 2:
(SEQ ID NO: 23)
5'-AGCCATGGCCGGCTGGGCCGCGAGTAATAAC-3'

(SEQ ID NO: 25)
CGCGGCCGCCACCATCATCACCACCATTAATAGcactagtcaagaggatc cggctgctaacaaagcccgaaaggaagctgagttggctgctgccaccgct gagcaataactagcataaccccttggggcctctaaacgggtcttgagggg ttttttgctgaaaggaggaactatatccggatgaattccgtgtattctat agtgtcacctaaatcgtatgtgtatgatacataaggttatgtattaattg tagccgcgttctaacgacaatatgtacaagcctaattgtgtagcatctgg cttactgaagcagaccctatcatctctctcgtaaactgccgtcagagtcg gtttggttggacgaaccttctgagtttctggtaacgccgtcccgcacccg gaaatggtcagcgaaccaatcagcagggtcatcgctagccagatcctcta cgccggacgcatcgtggccggcatcaccggcgccacaggtgcggttgctg gcgcctatatcgccgacatcaccgatggggaagatcgggctcgccacttc gggctcatgagcgcttgtttcggcgtgggtatggtggcaggccccgtggc cgggggactgttgggcgccatctccttgcatgcaccattccttgcggcgg cggtgctcaacggcctcaacctactactgggctgcttcctaatgcaggag tcgcataagggagagcgtcgaatggtgcactctcagtacaatctgctctg atgccgcatagttaagccagccccgacacccgccaacacccgctgacgcg ccctgacgggcttgtctgctcccggcatccgcttacagacaagctgtgac cgtctccgggagctgcatgtgtcagaggttttcaccgtcatcaccgaaac gcgcgagacgaaagggcctcgtgatacgcctatttttataggttaatgtc atgataataatggtttcttagacgtcaggtggcacttttcggggaaatgt gcgcggaacccctatttgtttattttttctaaatacattcaaatatgtatc cgctcatgagacaataaccctgataaatgcttcaataatattgaaaaagg aagagtatgagtattcaacatttccgtgtcgcccttattcccttttttgc ggcattttgccttcctgtttttgctcacccagaaacgctggtgaaagtaa aagatgctgaagatcagttgggtgcacgagtgggttacatcgaactggat ctcaacagcggtaagatccttgagagttttcgccccgaagaacgttttcc aatgatgagcacttttaaagttctgctatgtggcgcggtattatcccgta ttgacgccgggcaagagcaactcggtcgccgcatacactattctcagaat gacttggttgagtactcaccagtcacagaaaagcatcttacggatggcat gacagtaagagaattatgcagtgctgccataaccatgagtgataacactg cggccaacttacttctgacaacgatcggaggaccgaaggagctaaccgct tttttgcacaacatgggggatcatgtaactcgccttgatcgttgggaacc ggagctgaatgaagccataccaaacgacgagcgtgacaccacgatgcctg tagcaatggcaacaacgttgcgcaaactattaactggcgaactacttact ctagcttcccggcaacaattaatagactggatggaggcggataaagttgc aggaccacttctgcgctcggcccttccggctggctggtttattgctgata aatctggagccggtgagcgtgggtctcgcggtatcattgcagcactgggg ccagatggtaagccctcccgtatcgtagttatctacacgacggggagtca ggcaactatggatgaacgaaatagacagatcgctgagataggtgcctcac tgattaagcattggtaactgtcagaccaagtttactcatatatactttag attgatttaaaacttcattttttaatttaaaaggatctaggtgaagatcct ttttgataatctcatgaccaaaatcccttaacgtgagttttcgttccact gagcgtcagacccgtagaaaagatcaaaggatcttcttgagatccttt tttctgcgcgtaatctgctgcttgcaaacaaaaaaaccaccgctaccagc ggtggtttgtttgccggatcaagagctaccaactctttttccgaaggtaa ctggcttcagcagagcgcagataccaaatactgttcttctagtgtagccg -continued
tagttaggccaccacttcaagaactctgtagcaccgcctacatacctcgc tctgctaatcctgttaccagtggctgctgccagtggcgataagtcgtgtc ttaccgggttggactcaagacgatagttaccggataaggcgcagcggtcg ggctgaacgggggttcgtgcacacagcccagcttggagcgaacgaccta caccgaactgagatacctacagcgtgagctatgagaaagcgccacgcttc ccgaagggagaaaggcggacaggtatccggtaagcggcagggtcggaaca ggagagcgcacgagggagcttccagggggaaacgcctggtatctttatag tcctgtcgggtttcgccacctctgacttgagcgtcgattttgtgatgct cgtcagggggcggagcctatggaaaaacgccagcaacgcggcctttta cggttcctggccttttgctggccttttgctcacatgttctttcctgcgtt atccctgattctgtggataaccgtattaccgcctttgagtgagctgata ccgctcgccgcagccgaacgaccgagcgcagcgagtcagtgagcgaggaa gcggaagagcgcccaatacgcaaaccgcctctocccgcgcgttggccgat tcattaatgcagctggcttatcgaaattaatacgactcactatagggaga cccaagctttatttcaaggagacagtcataATGaaatacctattgcctac ggcagccgctggattgttattactcgcggcccagccggccatggct DNAs other than the following two DNAs (I) and (II) were fragmented with a restriction enzyme DpnI (available from TOYOBO). In other words, the following two DNAs (I) and (II) were remained unchanged; however, the rest of the DNAs were fragmented.

(I) the DNA represented by SEQ ID NO: 21, and
(II) the DNA represented by SEQ ID NO: 25.

The DNA represented by SEQ ID NO: 21 was fused with the DNA represented by the SEQ ID NO: 25. In this way, the VHH antibody gene fragment was ligated into the vector pRA2(+).

The ligation solution (10 microliters) and *coli* bacteria JM109 (available from Takara Bio, 100 microliters) were mixed on an ice. The mixture solution was left at rest on the ice for thirty minutes. Then, the mixture solution was heated at temperature of 42 Celsius degrees for forty five minutes. Finally, the mixture solution was left at rest on the ice for three minutes. This procedure is known as a general heat shock method.

After the incubation at a temperature of 37 degrees Celsius for one hour with shaking, all the amount of the mixture solution was distributed onto a LBA culture medium containing ampicillin at a concentration of 100 micrograms/milliliter. The LBA culture medium was left at rest overnight at temperature of 37 Celsius degrees.

Three colonies were selected from among the colonies formed on the LBA culture medium. The selected three colonies were incubated in the LBA culture medium (3 milliliters).

The plasmids contained in the incubated *coli* bacteria were extracted from the LBA culture medium using a plasmid extraction kit (available from Sigma, trade name: Gene Elute Plasmid Mini Kit). In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to be formed as planned.

*Coli* bacteria (Competent Cell BL21 (DE3) pLysS, available from Life technologies Company) were transfected with the selected plasmids.

An LBA culture medium (1 microliter) was injected to the solution containing the transfected *coli* bacteria. Then, the *coli* bacteria were rescued at temperature of 37 Celsius degrees for one hour, while shaken at 213 rpm.

Then, the *coli* bacteria solution was collected. The collected *coli* bacteria solution (1 milliliter) was distributed onto a LBA culture medium. The LBA culture medium was left at rest overnight at temperature of 37 Celsius degrees.

One colony was selected from among the colonies formed in the LBA culture medium. The selected colony was picked up with a toothpick. The picked-up colony was incubated in a LBA culture medium (3 milliliters) at temperature of 37 Celsius degrees, while shaken at 213 rpm. In this way, a culture liquid was obtained.

In addition, the culture liquid (3 milliliters) was mixed with a LBA culture medium (1,000 milliliters). Until the absorbance of the mixture solution at a wavelength of 600 nanometers was 0.6, the mixture solution was shaken at 120 rpm at temperature of 28 Celsius degrees.

After the absorbance was 0.6, an isopropylthiogalactoside solution (hereinafter, referred to as "IPTG solution") was added to the mixture solution. The final concentration of the IPTG solution was 0.5 mM. The *coli* bacteria contained in the mixture solution were incubated at temperature of 20 Celsius degrees for overnight. In order to collect the thus-incubated *coli* bacteria, the mixture solution was subject to centrifugation at 6,000 rpm for ten minutes at temperature of 4 Celsius degrees.

The collected *coli* bacteria were mixed with a mixture solvent containing 50 mM Tris-HCl, 500 mM NaCl, and 5 mM imidazole. The mixture solvent had a volume of 50 milliliters. The *coli* bacteria contained in the mixture solution was disintegrated with an ultrasonic wave.

The disintegration liquid containing *coli* bacteria was subject to centrifugation at 40,000 g for thirty minutes at temperature of 4 Celsius degrees to obtain an eluate. The supernatant was collected. The collected supernatant was filtered through a 0.45-micrometer filter.

The filtrate was purified with Ni-NTA-Agarose (available from QIAGEN) in accordance with recommended protocol. Upon the purification, an elution buffer having a total amount of 3 microliters was used for 1 milliliter of Ni-NTA-Agarose.

Furthermore, the eluate containing the anti-NP antibody was purified with a column chromatography (available from General Electric Company, trade name: Akita purifier). In this way, a solution containing the anti-NP antibody was obtained.

The anti-NP antibody contained in the thus-obtained solution was quantified with an absorption spectrometer (available from Scrum Inc., trade name: nanodrop) on the basis of the absorption measurement value at a wavelength of 280 nanometers. As a result, the concentration of the anti-NP antibody was 2.32 milligrams/milliliter.

(D-1) Surface Plasmon Resonance Evaluation of Anti-NP Antibody Using Recombinant NP The anti-NP antibody was evaluated as below with a recombinant NP and a surface plasmon resonance evaluation device. The details of the surface plasmon resonance (hereinafter, referred to as "SPR") will be described below.

SPR evaluation device: T200 (available from GE Healthcare)

Immobilization buffer: PBS containing 0.05% of Tween 20

Running buffer: PBS containing 0.05% of Tween 20
Sensor chip: CM5 (available from GE Healthcare)
Immobilization reagents: N-Hydroxysuccinimide (NHS) and N-[3-(Dimethylamino)propyl]-N'-ethylcarbodiimide (EDC)
Anti-Flag antibody: Monoclonal ANTI-FLAG antibody (available from SIGMA)
NP: recombinant nucleoprotein (NP) protein derived from influenza virus H1N1 to which a Flag tag was fused and which was prepared using baculovirus The anti-Flag antibody was immobilized in accordance with the wizard included in the control software of the SPR evaluation device T200. For the immobilization of the anti-Flag antibody, an acetic acid solution having a pH of 5.0 was used.

The anti-NP antibody consisting of the amino acid sequence represented by SEQ ID NO: 08 was used as an analyte. In the first to seven analyses, the concentrations of the anti-BP antibody contained in the running buffer were adjusted to 0.195 nM, 0.39 nM, 0.78 nM, 1.56 nM, 3.125 nM, 6.25 nM, and 12.5 nM, respectively. First, the recombinant intranuclear proteins were captured with the anti-Flag antibodies. Then, the anti-NP antibodies were supplied. In this way, the anti-NP antibodies were evaluated. FIGS. 3A-3G are graphs showing an evaluation result outputted from the SPR evaluation device T200. The dissociation constant Kd was calculated using the evaluation software (available from GE Healthcare). As a result, the dissociation constant Kd was 0.236 nM.

(D-2) Evaluation of Cross Reactivity to Other Influenza Virus Subtype by ELISA

Next, in order to evaluate binding ability of the VHH antibody consisting of the amino acid sequence represented by SEQ ID NO: 08 to recombinant nucleoproteins (namely, NP) derived from influenza subtype viruses type A H2N2, H3N2, and H7N9, the binding ability to the recombinant intranuclear proteins was evaluated with an ELSA measurement method.

A solution containing a recombinant nucleoprotein derived from influenza viruses subtype A H1N1 (available from Sino Biological Company, trade name: 11675-V08H) was prepared at a concentration of 500 micrograms/milliliter.

Similarly, four solutions containing recombinant nucleoproteins derived from influenza viruses subtype A H1N1, H2N2, H3N2, and H7N9 (available from Sino Biological Company, trade name: 40205-V08H, 40033-V08H, 40208-V08H, and 40111-V08H) were prepared at a concentration of 500 micrograms/milliliter, respectively.

Furthermore, a solution containing a recombinant nucleoprotein (available from ORLA) derived from influenza viruses subtype B was prepared at a concentration of 500 micrograms/milliliter. Hereinafter, the six solutions are referred to as "Solution group A".

a part of each of the six solutions included in the solution group A was diluted 50 fold with a PBS containing both of 5% skim milk (available from Wako Pure Chemical Industries Ltd.) and 0.05% of tween 20 (hereinafter, this PBS is referred to as "skim-milk-containing PBST"). In this way, a diluted solution group B (Concentration: 10 micrograms/milliliter) including six diluted solutions of the recombinant NP was obtained.

A part of each of the six solutions included in the diluted solution group B was diluted 10-fold again with the skim-milk-containing PBST. In this way, a diluted solution group C (Concentration: 1 microgram/milliliter) including six diluted solutions of the recombinant NP was obtained. This was repeated to obtain a diluted solution group D (Concentration: 0.1 microgram/milliliter), a diluted solution group E (Concentration: 0.01 microgram/milliliter), a diluted solution group F (Concentration: 0.001 microgram/milliliter), a diluted solution group G (Concentration: $1 \times 10^{-4}$ microgram/milliliter), and a diluted solution group H (Concentration: $1 \times 10^{-5}$ microgram/milliliter).

The solution containing the VHH antibody consisting of the amino acid sequence represented by SEQ ID NO: 08 (concentration: 5 micrograms/milliliter) was injected to the wells of 96-well microplate (Maxisorp, Nunc). Each of the wells contained 200 microliters of the solution. The 96-well plate was left at rest at room temperature for two hours to immobilize the virus in the wells.

The skim-milk-containing PBST was injected in each well to block the virus. The volume of the PBST injected to each well was 250 microliters. The 96-well plate was left at rest at room temperature for three hours.

PBST containing 0.05% tween 20 was injected in each well to wash the wells. The PBST had a pH of 7.4. The volume of the PBS injected to each well was 200 microliters. This was repeated twice.

Each of the diluted solutions of the recombinant NP included in the diluted solution groups B-H were injected into each well. As a reference, the skim-milk-containing PBST was injected to another well. This well including the skim-milk-containing PBST only was used as a reference to remove a background upon measurement. The volume of the solutions injected in each well was 100 microliters. The 96-well plate was left at rest at room temperature. In this way, the recombinant NPs contained in the solutions B-G was bound to the anti-NP VHH antibodies contained in the wells. The 96-well plate was left at rest at room temperature for one hour.

PBS containing 0.05% tween 20 was injected in each well to wash the wells. The PBS had a pH of 7.4. The volume of the PBS injected to each well was 200 microliters. This was repeated five times.

The anti-NP anti body (available from abcam company, trade name: ab110661) was diluted with the PBST containing 0.05% tween 20 (concentration: 5 micrograms/milliliter), and injected to each well. The volume of the PBST injected to each well was 100 microliters. In this way, the anti-NP antibody was bound to the recombinant NPs contained in the wells. The 96-well plate was left at rest at room temperature for one hour.

PBS containing 0.05% tween 20 was injected in each well to wash the wells. The PBS had a pH of 7.4. The volume of the PBS injected to each well was 200 microliters. This was repeated five times.

Labelled antibodies (available from Santa Cruz company, trade name: goat anti-mouse IgG-HRP) were diluted 20,000 fold with PBST containing 0.05% tween 20. The thus-diluted labelled antibodies was inject to each well (50 microliters/well). Then, the 96-well plate was left at rest for one hour.

PBS containing 0.05% tween 20 was injected in each well to wash the well Is. The PBS had a pH of 7.4. The volume of the PBS injected to each well was 200 microliters. This was repeated five times.

The color-producting agent (available from Thermo Scientific, trade name: 1-step ultra TMB-ELISA) was injected into each well (50 microliters/well). The 96-well plate was left at rest for thirty minutes to cause the color-producting agent to react with the antibody.

The color-stopping agent (available from ScyTek laboratories, trade name: TMB Stop Buffer) containing sulfuric acid and hydrochloric acid at a low concentration was injected into each well at a concentration of 50 microliters/well to cease the reaction.

The absorbance of the solution at a wavelength of 450 nanometers was measured. FIGS. 4A-4F are graphs showing the measurement result of the cross reactivity of the VHH antibody consisting of the amino acid sequence represented by SEQ ID NO: 08 with regard to the influenza virus type A H1N1 11675, H1N1 40205, H2N2, H3N2, H7N9, and the influenza virus type B, respectively.

As understood from FIGS. 4A-4F, the VHH antibody consisting of the amino acid sequence represented by SEQ ID NO: 08 has high cross reactivity to the recombinant intranuclear proteins derived from influenza viruses type A H1N1, H2N2, H3N2, H7N9. On the other hand, the VHH antibody consisting of the amino acid sequence represented by SEQ ID NO: 08 has low cross reactivity to the influenza virus type B.

INDUSTRIAL APPLICABILITY

The present invention provides a composite comprising a novel antibody capable of binding to the intranuclear protein of the influenza virus. The present invention also provides a detection device and a detection method using the composite comprising the novel antibody.

The invention claimed is:

1. An antibody that consists of an amino acid sequence, wherein said amino acid sequence consists of, in an N- to C-direction, the following structural domains:

N-FR1-CDR1-FR2-CDR2-FR3-CDR3-FR4-C wherein

FR denotes a framework region amino acid sequence and CDR denotes a complementary determining region amino acid sequence;

the CDR1 consists of an amino acid sequence represented by RTIFNPNVMG (SEQ ID NO: 01);

the CDR2 consists of an amino acid sequence represented by DISLSGSTNYADSVKG (SEQ ID NO: 02);

the CDR3 consists of an amino acid sequence represented by NAISGAPGRY (SEQ ID NO: 03);

the antibody is capable of binding to an influenza virus type A;

the influenza virus type A is at least one kind selected from the group consisting of H1N1, H2N2, H3N2, and H7N9;

the FR1, the FR2, the FR3, and the FR4 consist of amino acid sequences represented by QVQLVESGGGLVQAGGSLRLSCAAS (SEQ ID NO: 04), WYRQAPGKQRELVA (SEQ ID NO: 05), RFTISRDNAKNTMYLQMNSLKPEDTAVYYCNT (SEQ ID NO: 06), and WGQGAQVTVSS (SEQ ID NO: 07), respectively.

2. A bead, comprising:

an antibody, wherein the antibody is bound to a surface of the bead; and the antibody that consists of an amino acid sequence, wherein said amino acid sequence consists of, in an N- to C-direction, the following structural domains:

N-FR1-CDR1-FR2-CDR2-FR3-CDR3-FR4-C
wherein
FR denotes a framework region amino acid sequence and CDR denotes a complementary determining region amino acid sequence;
the CDR1 consists of an amino acid sequence represented by RTIFNPNVMG (SEQ ID NO: 01);
the CDR2 consists of an amino acid sequence represented by DISLSGSTNYADSVKG (SEQ ID NO: 02);
the CDR3 consists of an amino acid sequence represented by NAISGAPGRY (SEQ ID NO: 03);
the antibody is capable of binding to an influenza virus type A;
the influenza virus type A is at least one kind selected from the group consisting of H1N1, H2N2, H3N2, and H7N9;
the FR1, the FR2, the FR3, and the FR4 consist of amino acid sequences represented by QVQLVES-GGGLVQAGGSLRLSCAAS (SEQ ID NO: 04), WYRQAPGKQRELVA (SEQ ID NO: 05), RFTISRD-NAKNTMYLQMNSLKPEDTAVYYCNT (SEQ ID NO: 06), and WGQGAQVTVSS (SEQ ID NO: 07), respectively.

3. A bead, comprising:
an antibody,
wherein
the antibody is bound to a surface of the bead; and
the antibody consists of the amino acid sequence represented by SEQ ID NO: 08.

4. An antibody consisting of the amino acid sequence represented by SEQ ID NO: 08.

* * * * *